(12) United States Patent
Ise et al.

(10) Patent No.: US 8,349,473 B2
(45) Date of Patent: Jan. 8, 2013

(54) ORGANIC ELECTROLUMINESCENT DEVICE

(75) Inventors: Toshihiro Ise, Kanagawa (JP); Wataru Sotoyama, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 380 days.

(21) Appl. No.: 12/731,230

(22) Filed: Mar. 25, 2010

(65) Prior Publication Data

US 2010/0244006 A1    Sep. 30, 2010

(30) Foreign Application Priority Data

Mar. 25, 2009    (JP) .................................. 2009-075189

(51) Int. Cl.
*H01L 51/54*    (2006.01)
*C07D 487/04*    (2006.01)

(52) U.S. Cl. ...................... 428/690; 428/917; 548/302.1
(58) Field of Classification Search .................... None
See application file for complete search history.

(56) References Cited

U.S. PATENT DOCUMENTS 6,303,238 B1    10/2001    Thompson et al.

FOREIGN PATENT DOCUMENTS

| JP | 2001-160488 A | 6/2001 |
| JP | 2001-357977 A | 12/2001 |
| WO | 00/57676 A1 | 9/2000 |

OTHER PUBLICATIONS

Kuzmenko et al., Khimiya Geterotsiklicheskikh Soedinenii, (12), pp. 1698-1705, (1992).*
Kuzmenko et al., Khimiya Geterotsiklicheskikh Soedinenii, (1), pp. 43-48, (1988).*
Hayashi et al., Nippon Shashin Gakkaishi, 71(2), pp. 75-80, (2008).*

* cited by examiner

*Primary Examiner* — Dawn L. Garrett
(74) *Attorney, Agent, or Firm* — Morgan, Lewis & Bockius, LLP

(57) ABSTRACT

An organic electroluminescent device is provided and includes: a cathode; an anode; and at least one organic layer between the cathode and the anode. The at least one organic layer includes a light emitting layer containing at least one light emitting material. A compound represented by the following formula (I) is contained in the at least one organic layer.

Formula (I):

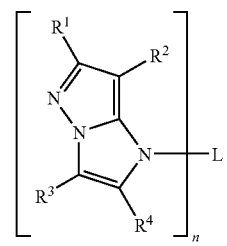

where n stands for an integer of 2 or greater, L represents an n-valent linking group, and $R^1$, $R^2$, $R^3$, and $R^4$ each independently represents a hydrogen atom or a substituent.

11 Claims, No Drawings

ORGANIC ELECTROLUMINESCENT DEVICE

This application is based on and claims priority under 35 U.S.C. §119 from Japanese Patent Application No. 2009-075189, filed Mar. 25, 2009, the entire disclosure of which is herein incorporated by reference.

BACKGROUND OF THE INVENTION

1. Field of the Invention

The present invention relates to an organic electroluminescent device that converts electric energy into light and emits the light and also a novel fused heterocyclic organic compound.

2. Description of the Related Art

Since organic electroluminescent devices (which may hereinafter be called "organic EL devices") are capable of emitting light with a high luminance at low voltage, they have been actively researched and developed. Organic electroluminescent devices have a pair of electrodes and an organic layer therebetween and utilize, for light emission, energy of the exciton generated as a result of recombination of electrons injected from the cathode and holes injected from the anode in the organic layer.

The devices have recently had improved efficiency by using phosphorescent materials. There are disclosed inventions relating to phosphorescent devices using an iridium complex or a platinum complex as a phosphorescent material (refer to, for example, U.S. Pat. No. 6,303,238 and WO00/57676). However, devices that can satisfy both high efficiency and high durability have not yet been developed.

JP-A-2001-160488 discloses an invention relating to an organic electroluminescent device containing a compound having, as a dopant, a skeleton represented by the following formula (A):

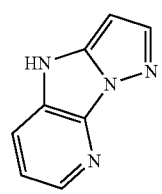

(A)

JP-A-2001-357977 discloses an invention relating to an organic electroluminescent device containing a compound that contains a heterocycle skeleton having at a fused position thereof a nitrogen atom and is represented by the following formula (B):

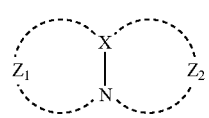

(B)

In formula (B), X represents a carbon atom or a nitrogen atom, and $Z_1$ and $Z_2$ each independently represents a group of atoms capable of forming a nitrogen-containing heterocycle.

However, JP-A-2001-160488 and JP-A-2001-357977 do not disclose a compound having a plurality of pyrazoloimidazole skeletons.

For increasing practical usability, organic electroluminescent devices should be excellent in both external quantum efficiency and running durability. There is therefore a demand for further improvement of the devices.

SUMMARY OF THE INVENTION

An object of an illustrative, non-limiting embodiment of the invention is to provide an organic electroluminescent device having high luminous efficiency and having high durability. Another object is to provide a compound that has a plurality of pyrazoloimidazole skeletons and is suited for providing the organic electroluminescent device.

As a result of investigation with a view to fulfilling the above-described objects, the present inventors have found that an organic electroluminescent device containing, in an organic layer thereof, a compound having a plurality of pyrazoloimidazole skeletons can fulfill the above-described objects. In short, according to an aspect of the invention, there are provided the following means.

[1] An organic electroluminescent device comprising:
   a cathode;
   an anode; and
   at least one organic layer between the cathode and the anode, the at least one organic layer including a light emitting layer containing at least one light emitting material,
   the device comprising, in the at least one organic layer, a compound represented by formula (I):

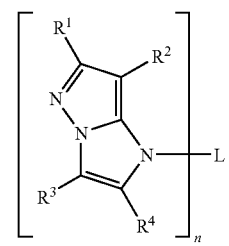

wherein n stands for an integer of 2 or greater, L represents an n-valent linking group, and $R^1$, $R^2$, $R^3$, and $R^4$ each independently represents a hydrogen atom or a substituent.

[2] The organic electroluminescent device as described in [1], wherein the compound represented by formula (I) is a compound represented by formula (II):

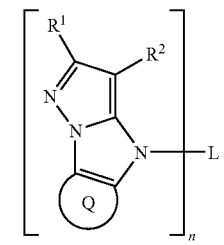

wherein n stands for an integer of 2 or greater, L represents an n-valent linking group, $R^1$ and $R^2$ each independently represents a hydrogen atom or a substituent, and Q represents a benzene ring or an aromatic heterocycle.

[3] The organic electroluminescent device as described in [2], wherein the compound represented by formula (II) is a compound represented by formula (III):

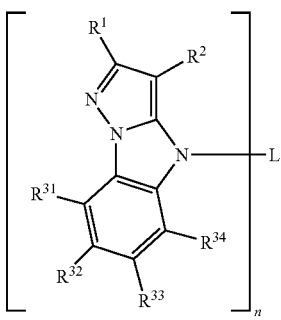

wherein n stands for an integer of 2 or greater, L represents an n-valent linking group, and $R^1$, $R^2$, $R^{31}$, $R^{32}$, $R^{33}$, and $R^{34}$ each independently represents a hydrogen atom or a substituent.

[4] The organic electroluminescent device as described in any one of [1] to [3], wherein n in formula (I) to (III) stands for an integer from 2 to 6.

[5] The organic electroluminescent device as described in any one of [1] to [4], wherein L in formula (I) to (III) represents a linking group including a benzene ring.

[6] The organic electroluminescent device as described in [3], wherein the compound represented by formula (III) is a compound represented by formula (IV):

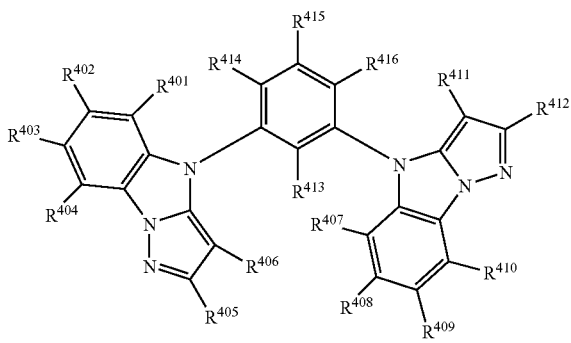

wherein $R^{401}$ to $R^{416}$ each independently represents a hydrogen atom or a substituent.

[7] The organic electroluminescent device as described in any one of [1] to [6], wherein the compound represented by any one of formula (I) to (III) is contained in the light emitting layer.

[8] The organic electroluminescent device as described in any one of [1] to [7], wherein the light emitting material includes a phosphorescent material.

[9] The organic electroluminescent device as described in [8], wherein the phosphorescent material is a platinum complex or an iridium complex.

[10] The organic electroluminescent device as described in [9], wherein the platinum complex has a tridentate ligand or a tetradentate ligand.

[11] The organic electroluminescent device as described in [10], wherein the platinum complex is represented by formula (C-1):

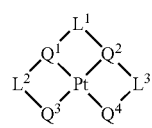

wherein $Q^1$, $Q^2$, $Q^3$, and $Q^4$ each independently represents a ligand coordinated to Pt, and $L^1$, $L^2$, and $L^3$ each independently represents a single bond or a divalent linking group.

[12] A compound represented by formula (IV):

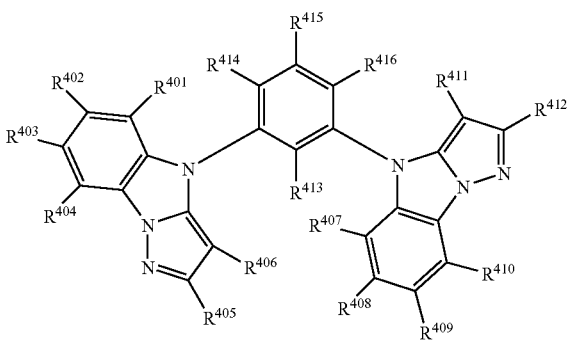

wherein $R^{401}$ to $R^{416}$ each independently represents a hydrogen atom or a substituent.

DETAILED DESCRIPTION OF THE EXEMPLARY EMBODIMENTS

An organic electroluminescent device according to an exemplary embodiment of the invention has both high external quantum efficiency and excellent durability. In addition, a compound according to an exemplary embodiment of the invention can be used to provide an organic electroluminescent device having both high external quantum efficiency and excellent durability.

Exemplary embodiments of the invention will be described. In the present specification, "$C_{k\text{-}l}$ group" means that the number of carbon atoms in the group is from k to l.

An organic electroluminescent device according to an exemplary embodiment of the invention includes: a cathode; an anode; and at least one organic layer between the cathode and the anode, the at least one organic layer including a light emitting layer containing at least one light emitting material. The device includes, in the at least one organic layer, a compound represented by formula (I):

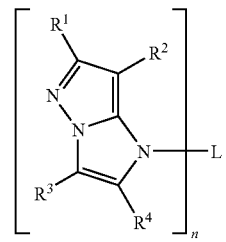

wherein n stands for an integer of 2 or greater, L represents an n-valent linking group, and $R^1$, $R^2$, $R^3$, and $R^4$ each independently represents a hydrogen atom or a substituent.

Described specifically, the organic electroluminescent device of the invention has at least one light emitting layer as an organic layer. It may have, as an organic layer other than the light emitting layer, a hole injection layer, a hole transport layer, an electron blocking layer, an exciton blocking layer, a hole blocking layer, an electron transport layer, an electron injection layer, and a protective layer as needed. Such a layer may have a function of another layer in addition to its own function. Each of these layers may include a plurality of layers.

The organic electroluminescent device of the invention may make use of either light emission from an excited singlet state (fluorescence) or light emission from an excited triplet state (phosphorescence) but in view of luminous efficiency, that making use of phosphorescence is preferred.

The light emitting layer of the organic electroluminescent device of the invention preferably contains at least one light emitting material and at least one host material. The term "host material" as used herein means a material constituting the light emitting layer except the light emitting material. It means a material having at least one of a function of dispersing the light emitting material and keeping it in the light emitting layer, a function of receiving holes from an anode, a hole transport layer or the like, a function of receiving electrons from a cathode, an electron transport layer or the like, a function of transporting holes and/or electrons, a function of providing a site for recombination of holes and electrons, a function of transferring the energy of an exciton produced by the recombination to the light-emitting material, and a function of transporting holes and/or electrons to the light emitting material.

The compound of the invention may be contained in any of the organic layers. It may also be contained in two or more of the organic layers but is contained preferably in a hole injection layer, a hole transport layer, an electron blocking layer, the light emitting layer, a hole blocking layer, an electron transport layer, or an electron injection layer; more preferably in the light emitting layer, a hole blocking layer, an electron transport layer, or an electron injection layer; particularly preferably in the light emitting layer; most preferably in the light-emitting layer as a host material. When the compound of the invention is contained as a host material in the light-emitting layer, the content of it in the light emitting layer is preferably from 50 mass % (weight %) to 99.9 mass %, more preferably from 60 mass % to 99 mass %. When the compound of the invention is contained in the hole injection layer, hole transport layer, electron blocking layer, hole blocking layer, electron transport layer, or electron injection layer, the content of the invention compound in each layer is preferably from 70 mass % to 100 mass %, more preferably from 85 mass % to 100 mass %, most preferably from 99 mass % to 100 mass %. Furthermore, when the device has two or more electron transport layers, it is preferred that one of them contains the compound of the invention.

The compound represented by formula (I) is described below.

Formula (I):

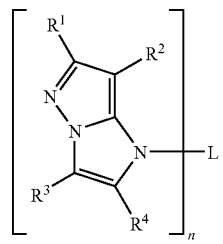

In the formula (I), n stands for an integer of 2 or greater, L represents an n-valent linking group, and $R^1$, $R^2$, $R^3$, and $R^4$ each independently represents a hydrogen atom or a substituent.

n stands for an integer of 2 or greater, preferably from 2 to 6, more preferably from 2 to 4, particularly preferably 2 or 3, particularly preferably 2.

$R^1$, $R^2$, $R^3$, and $R^4$ each independently represents a hydrogen atom or a substituent. As the substituent represented by $R^1$, $R^2$, $R^3$, and $R^4$, those exemplified in the following substituent group A can be used independently.

An organic electroluminescent device is excellent in efficiency and running durability when it contains, in the organic layer thereof, the compound represented by the formula (1).

(Substituent Group A)

Examples of the substituent belonging to Substituent group A include alkyl groups (preferably $C_{1-30}$, more preferably $C_{1-20}$, particularly preferably $C_{1-10}$ alkyl groups such as methyl, ethyl, isopropyl, tert-butyl, n-octyl, n-decyl, n-hexadecyl, cyclopropyl, cyclopentyl, and cyclohexyl), alkenyl groups (preferably $C_{2-30}$, more preferably $C_{2-20}$, particularly preferably $C_{2-10}$ alkenyl groups such as vinyl, allyl, 2-butenyl, and 3-pentenyl), alkynyl groups (preferably $C_{2-30}$, more preferably $C_{2-20}$, particularly preferably $C_{2-10}$ alkynyl groups such as propargyl and 3-pentynyl), aryl groups (preferably $C_{6-30}$, more preferably $C_{6-20}$, particularly preferably $C_{6-12}$ aryl groups such as phenyl, p-methylphenyl, naphthyl, and anthranyl), amino groups (preferably $C_{0-30}$, more preferably $C_{0-20}$, particularly preferably $C_{0-10}$ amino groups such as amino, methylamino, dimethylamino, diethylamino, dibenzylamino, diphenylamino, and ditolylamino), alkoxy groups (preferably $C_{1-30}$, more preferably $C_{1-20}$, particularly preferably $C_{1-10}$ alkoxy groups such as methoxy, ethoxy, butoxy, and 2-ethylhexyloxy), aryloxy groups (preferably $C_{6-30}$, more preferably $C_{6-20}$, particularly preferably $C_{6-12}$ aryloxy groups such as phenyloxy, 1-naphthyloxy, and 2-naphthyloxy), heterocyclic oxy groups (preferably $C_{1-30}$, more preferably $C_{1-20}$, particularly preferably $C_{1-12}$ heterocyclic oxy groups such as pyridyloxy, pyrazyloxy, pyrimidyloxy, and quinolyloxy), acyl groups (preferably $C_{2-30}$, more preferably $C_{2-20}$, particularly preferably $C_{2-12}$ acyl groups such as acetyl, benzoyl, formyl, and pivaloyl), alkoxycarbonyl groups (preferably $C_{2-30}$, more preferably $C_{2-20}$, particularly preferably $C_{2-12}$ alkoxycarbonyl groups such as methoxycarbonyl and ethoxycarbonyl), aryloxycarbonyl groups (preferably $C_{7-30}$, more preferably $C_{7-20}$, especially preferably $C_{7-12}$ aryloxycarbonyl groups such as phenyloxycarbonyl), acyloxy groups (preferably $C_{2-30}$, more preferably $C_{2-20}$, particularly preferably $C_{2-10}$ acyloxy groups such as acetoxy and benzoyloxy), acylamino groups (preferably $C_{2-30}$, more preferably $C_{2-20}$, particularly preferably $C_{2-10}$ acylamino groups such as acetylamino and benzoylamino), alkoxycarbonylamino groups (preferably $C_{2-30}$, more preferably $C_{2-20}$, particularly preferably $C_{2-12}$ alkoxycarbonylamino groups such as methoxycarbonylamino), aryloxycarbonylamino groups (preferably $C_{7-30}$, more preferably $C_{7-20}$, particularly preferably $C_{7-12}$ aryloxycarbonylamino groups such as phenyloxycarbonylamino), sulfonylamino groups (preferably $C_{1-30}$, more preferably $C_{1-20}$, particularly preferably $C_{1-12}$ sulfonylamino groups such as methanesulfonylamino and benzenesulfonylamino), sulfamoyl groups (preferably $C_{0-30}$, more preferably $C_{0-20}$, particularly preferably $C_{0-12}$ sulfamoyl groups such as sulfamoyl, methylsulfamoyl, dimethylsulfamoyl, and phenylsulfamoyl), carbamoyl groups (preferably $C_{1-30}$, more preferably $C_{1-20}$, particularly preferably $C_{1-12}$ carbamoyl groups such as carbamoyl, methylcarbamoyl, diethylcarbamoyl, and phenylcarbamoyl), alkylthio groups (preferably $C_{1-30}$, more preferably $C_{1-20}$, particularly preferably $C_{1-12}$ alkylthio groups such as methylthio and ethylthio), arylthio groups (preferably $C_{6-30}$, more preferably $C_{6-20}$, particularly preferably $C_{6-12}$ arylthio groups such as phenylthio), heterocyclic thio groups (preferably $C_{1-30}$, more preferably $C_{1-20}$, particularly preferably $C_{1-12}$ heterocyclic thio groups such as pyridylthio, 2-benzimidazolylthio, 2-benzoxazolylthio, and 2-benzothiazolylthio), sulfonyl groups (preferably $C_{1-30}$, more preferably $C_{1-20}$, particularly preferably $C_{1-12}$ sulfonyl groups such as mesyl and tosyl), sulfinyl groups (preferably $C_{1-30}$, more preferably $C_{1-20}$, particularly preferably $C_{1-12}$ sulfinyl groups such as methanesulfinyl and benzenesulfinyl), ureido groups (preferably $C_{1-30}$, more preferably $C_{1-20}$, particularly preferably $C_{1-12}$ ureido groups such as ureido, methylureido, and phenylureido), phosphoric acid amide groups (preferably $C_{1-30}$, more preferably $C_{1-20}$, particularly preferably $C_{1-12}$ phosphoric acid amide groups such as diethylphosphoric acid amide and phenylphosphoric acid amide), a hydroxyl group, a mercapto group, halogen atoms (such as fluorine, chlorine, bromine, and iodine), a cyano group, a sulfo group, a carboxyl group, a nitro group, a hydroxamic acid group, a sulfino group, a hydrazino group, an imino group, heterocyclic groups (preferably $C_{1-30}$, more preferably $C_{1-12}$ heterocyclic groups embracing aromatic heterocyclic groups, with the heteroatom being, for example, a nitrogen atom, an oxygen atom, a sulfur atom, a phosphorus atom, a silicon atom, a selenium atom, or a tellurium atom; and more specifically, pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, carbazolyl, azepinyl, and silolyl), silyl groups (preferably $C_{3-40}$, more preferably $C_{3-30}$, particularly preferably $C_{3-24}$ silyl groups such as trimethylsilyl and triphenylsilyl), silyloxy groups (preferably $C_{3-40}$, more preferably $C_{3-30}$, particularly preferably $C_{3-24}$ silyloxy groups such as trimethylsilyloxy and triphenylsilyloxy), and phosphoryl groups (such as diphenylphosphoryl and dimethylphosphoryl). These substituents may be substituted further with another substituent and the another substituent can be selected from Substituent group A described above.

In the invention, the number of carbon atoms "$C_{k-1}$" of the substituent such as the alkyl group also applies to the case where the substituent such as alkyl group may be substituted with another substituent and the number includes the number of carbon atoms of the another substituent.

$R^1$ and $R^2$ are each preferably an alkyl group, an aryl group, an amino group, an alkoxy group, an aryloxy group, a heterocyclic oxy group, an alkylthio group, an arylthio group, a heterocyclic thio group, a halogen atom (such as fluorine, chlorine, bromine, or iodine), a cyano group, a heterocyclic group, or a silyl group, more preferably an alkyl group, an aryl group, a fluoro group, a cyano group, a heterocyclic group, or a silyl group, more preferably an alkyl group, an aryl group, a fluoro group, or a cyano group, still more preferably an alkyl group or a fluoro group.

It is preferred that $R^3$ and $R^4$ are each an alkyl group, an aryl group, an amino group, an alkoxy group, an aryloxy group, a heterocyclic oxy group, an alkylthio group, an arylthio group, a heterocyclic thio group, a halogen atom (such as fluorine, chlorine, bromine, or iodine), a cyano group, a heterocyclic group, or a silyl group, or are groups that may be coupled to form an aromatic ring or aromatic heterocyclic group; more preferred that $R^3$ and $R^4$ are each an alkyl group, an aryl group, a fluoro group, a cyano group, a heterocyclic group, or a silyl group, or are groups that may be coupled to form an aromatic ring or aromatic heterocyclic group; still more preferred that $R^3$ and $R^4$ are each an alkyl group, an aryl group, a fluoro group, or a cyano group, or are groups that may be coupled to form an aromatic ring or aromatic heterocyclic group; still more preferred that $R^3$ and $R^4$ are each an alkyl group or are groups that may be coupled to form an aromatic ring or aromatic heterocyclic group; particularly preferred that $R^3$ and $R^4$ are groups that may be coupled to form a benzene ring.

L represents an n-valent linking group.

As the linking group represented by L, those including C, O, N, S, Si, Ge, or P are preferred.

The linking group is more preferably a linking group having an aromatic ring, still more preferably a linking group composed of an aromatic ring, a linking group composed of an aromatic ring and N, a linking group composed of an aromatic ring and O, a linking group composed of an aromatic ring and S, or a linking group composed of an aromatic ring and Si; still more preferably any of linking groups described below. In the following linking group, R represents an arbitrary group selected from Substituent group A. The following linking group may have a substituent and as the substituent, those exemplified in Substituent group A can be used.

When the linking groups are divalent ones:

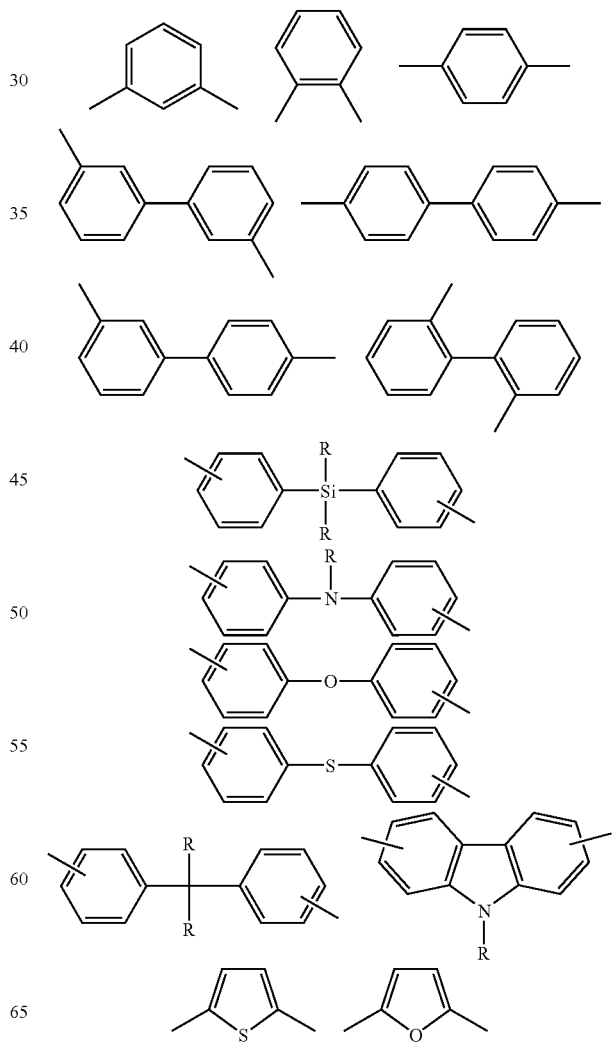

-continued

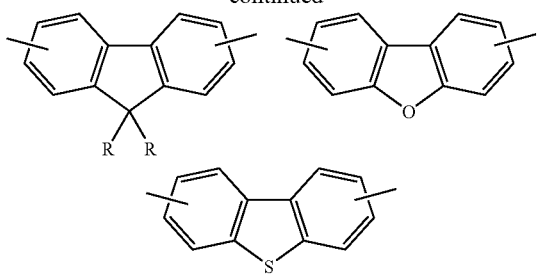

When the linking groups are trivalent ones:

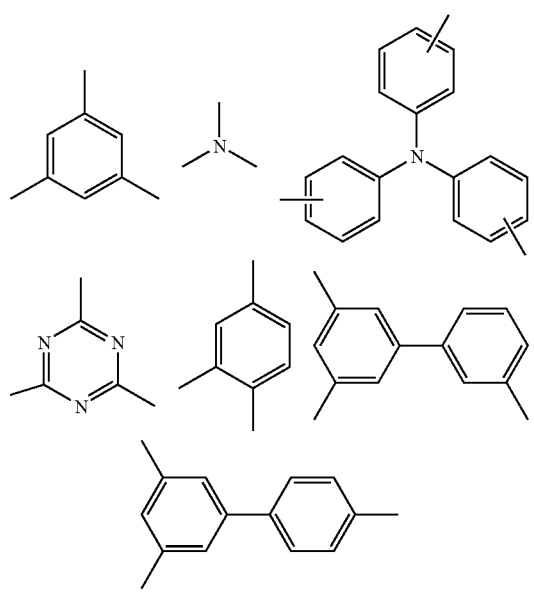

When the linking groups are tetravalent ones:

-continued

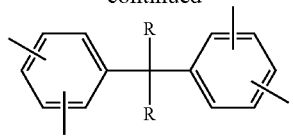

When the linking groups are pentavalent ones:

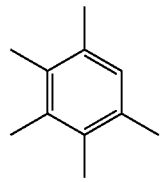

When the linking groups are hexavalent ones:

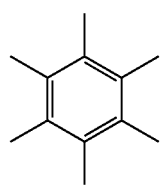

Among them, L represents particularly preferably a linking group having, as a constituent element thereof, only a substituted or unsubstituted benzene ring.

When the linking group L is a benzene ring, linkage at the m-position is preferred from the standpoint of keeping a high triplet energy.

L may have a substituent and examples of the substituent include those selected from Substituent group A described above.

The substituent of L is preferably a hydrogen atom, an alkyl group, an alkyl halide group, an aryl group, an aromatic heterocyclic group, an alkoxy group, an amino group, a silyl group, a fluorine group, or a cyano group; more preferably a hydrogen atom, an alkyl group, an alkyl fluoride group, an aryl group, an aromatic heterocyclic group, or a cyano group; still more preferably a hydrogen atom, an alkyl group, an alkyl fluoride group, an aryl group, or a cyano group; particularly preferably a hydrogen atom, an alkyl group, an alkyl fluoride group, or a cyano group; most preferably a hydrogen atom.

The compound represented by the formula (I) is more preferably a compound represented by formula (II) in consideration of an ionization potential in a thin film, control of the electron affinity, and spread of the π electron system from the viewpoint of a charge transport property and running durability of the device. The compound represented by the formula (II) will next be described.

Formula (II):

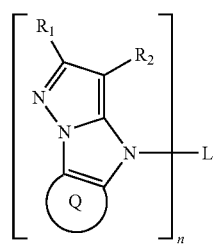

In the formula (II), n stands for an integer of 2 or greater, L represents an n-valent linking group, $R^1$ and $R^2$ each represents a hydrogen atom or a substituent, and Q represents a benzene ring or an aromatic heterocycle.

n, L, $R^1$, and $R^2$ in the formula (II) have the same meanings as described in the formula (I), respectively, and their preferred ranges are also the same.

Q represents a benzene ring or an aromatic heterocycle.

Examples of the aromatic heterocycle represented by Q include nitrogen-containing 5-membered heterocycles, nitrogen-containing 6-membered heterocycles, oxygen-containing 5-membered heterocycles, and sulfur-containing 5-membered heterocycles. Specific examples include a pyridine ring, a pyrazine ring, a pyrimidine ring, a pyridazine ring, a pyrrole ring, a pyrazole ring, an imidazole ring, a furan ring, a thiophene ring, an oxazole ring, an isoxazole ring, a thiazole ring, an isothiazole ring, a selenophene ring, and a tellurophene ring. In consideration of stability of the mother nucleus of the aromatic ring, ionization potential in a thin film, control of the electron affinity, and spread of the π electron system from the viewpoint of a charge transport property and running durability of the device, Q represents preferably a benzene ring, a pyridine ring, a pyrazine ring, a pyrrole ring, a pyrazole ring, an imidazole ring, a 1,2,4-triazole ring, a furan ring, a thiophene ring, an oxazole ring, a thiazole ring, a 1,3,4-oxadiazole ring, and a 1,3,4-thiadiazole ring; more preferably a benzene ring, a pyridine ring, a pyrimidine ring, a pyrazine ring, a 1,3,5-triazine ring, a pyrazole ring, an imidazole ring, an oxazole ring, a thiazole ring, or a thiophene ring; still more preferably a benzene ring, a pyridine ring, a pyrimidine ring, a pyrazine ring, an imidazole ring, a pyrazole ring, an oxazole ring, or a thiazole ring; still more preferably a benzene ring, a pyridine ring, or a pyrazine ring; particularly preferably a benzene ring.

Q may have a substituent and examples of the substituent include those selected from Substituent group A. When Q has a plurality of substituents, these substituents may be the same or different.

The benzene ring or aromatic heterocycle represented by Q may form a fused ring with another ring. Examples of the ring to be fused include a benzene ring, a pyridine ring, a pyrazine ring, a pyrimidine ring, a pyridazine ring, a pyrrole ring, a pyrazole ring, an imidazole ring, a 1,2,4-triazole ring, an oxazole ring, a thiazole ring, a furan ring, a thiophene ring, a selenophene ring, a tellurophene ring, a silole ring, a germole ring, and a phosphole ring. In consideration of stability of the mother nucleus of the aromatic ring, ionization potential in a thin film, control of the electron affinity, and spread of the π electron system from the viewpoint of a charge transport property and running durability of the device, the ring to be fused is preferably a benzene ring, a pyridine ring, a pyrazine ring, an imidazole ring, an oxazole ring, or a thiophene ring, more preferably a benzene ring, a pyrazine ring, or an imidazole ring, still more preferably a benzene ring or a pyridine ring.

The above-described substituent or fused ring may have a substituent further or fused with another ring further.

The compound represented by the formula (I) or (II) is preferably a compound represented by formula (III) in consideration of stability of the mother nucleus of the aromatic ring, ionization potential in a thin film, control of the electron affinity, and spread of the π electron system from the viewpoint of the π charge transport property and running durability of the device. The compound represented by the formula (III) will next be described.

Formula (III):

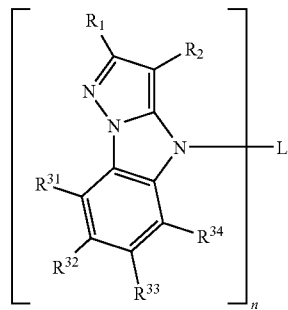

In formula (III), n stands for an integer of 2 or greater, L represents an n-valent linking group, and $R^1$, $R^2$, $R^{31}$, $R^{32}$, $R^{33}$, and $R^{34}$ each independently represents a hydrogen atom or a substituent.

n, L, $R^1$, and $R^2$ in formula (III) have the same meanings as described above in the formula (I) and preferred ranges of them are also the same.

$R^{31}$, $R^{32}$, $R^{33}$, and $R^{34}$ each independently represents a hydrogen atom or a substituent.

As the substituent represented by $R^{31}$, $R^{32}$, $R^{33}$, or $R^{34}$, those exemplified in Substituent group A can be used independently.

$R^{31}$, $R^{32}$, $R^{33}$, and $R^{34}$ are each preferably a hydrogen atom, an alkyl group, an alkyl halide group, an aryl group, an aromatic heterocyclic group, an alkoxy group, an amino group, a silyl group, a fluorine group, or a cyano group; more preferably a hydrogen atom, an alkyl group, an alkyl fluoride group, an aryl group, an aromatic heterocyclic group, or a cyano group; more preferably a hydrogen atom, an alkyl group, an alkyl fluoride group, an aryl group, or a cyano group; particularly preferably a hydrogen atom, an alkyl group, an alkyl fluoride group, or a cyano group; most preferably a hydrogen atom.

The compounds represented by any of the formulae (I) to (III) is preferably a compound represented by formula (IV) in consideration of an ionization potential in a thin film, control of the electron affinity, and spread of the π electron system from the viewpoint of a charge transport property and running durability of the device. The compound represented by the formula (IV) will next be described.

Formula (IV):

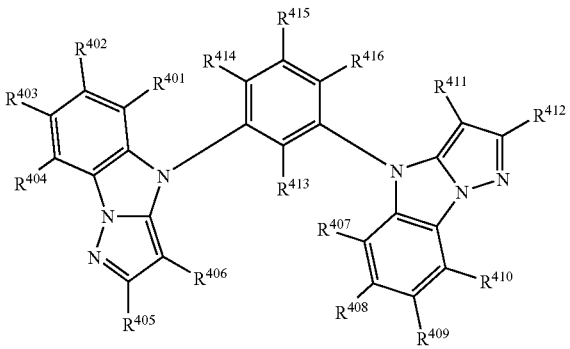

In the formula (IV), $R^{401}$ to $R^{416}$ each independently represents a hydrogen atom or a substituent.

$R^{401}$ to $R^{416}$ each independently represents a hydrogen atom or a substituent. As the substituent represented by $R^{401}$ to $R^{416}$, those exemplified in Substituent group A can be used independently.

Preferred ranges of $R^{405}$, $R^{406}$, $R^{411}$, and $R^{412}$ are similar to the preferred ranges of $R^1$ and $R^2$ in the formula (I).

Preferred ranges of $R^{401}$ to $R^{404}$ and $R^{407}$ to $R^{410}$ are similar to the preferred ranges of $R^{31}$, $R^{32}$, $R^{33}$ and $R^{34}$ in the formula (III).

$R^{413}$ to $R^{416}$ are each preferably a hydrogen atom, an alkyl group, an aryl group, an amino group, an alkoxy group, an aryloxy group, a heterocyclic oxy group, an alkylthio group, an arylthio group, a heterocyclic thio group, a halogen atom (such as fluorine, chlorine, bromine, or iodine), a cyano group, a heterocyclic group, or a silyl group; more preferably a hydrogen atom, an alkyl group, an aryl group, a fluoro group, a cyano group, a heterocyclic group, or a silyl group; still more preferably a hydrogen atom, an alkyl group, an aryl group, a fluoro group, or a cyano group; particularly preferably a hydrogen atom, an alkyl group, or a fluoro group; most preferably a hydrogen atom.

The compound represented by the formula (I) in the invention may be a low-molecular-weight compound, a polymer having a residue of the compound represented by the formula (I) which is coupled to the polymer main chain thereof (having preferably a weight average molecular weight of from 1000 to 5000000, more preferably from 5000 to 2000000, still more preferably from 10000 to 1000000), or a polymer having, as a main chain thereof, the structure of the compound represented by the formula (I) in the invention (having preferably a weight average molecular weight of from 1000 to 5000000, more preferably from 5000 to 2000000, still more preferably from 10000 to 1000000). The polymer compound may be a homopolymer or a copolymer with another polymer. When it is a copolymer, it may be a random copolymer or a block copolymer. When it is a copolymer, it may have, in the polymer thereof, a compound having a light emitting function and/or a compound having a charge transporting function.

<Compound Represented by Formula (IV)>

The invention also relates to a compound represented by formula (IV).

Formula (IV):

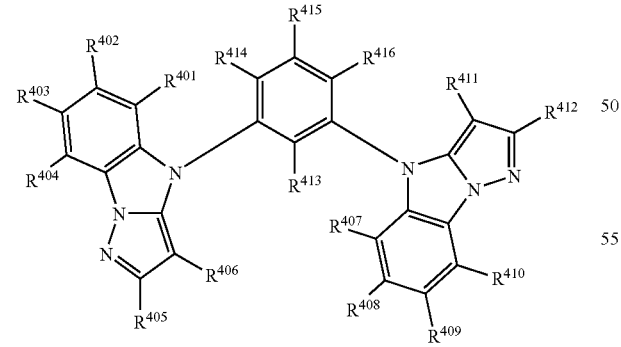

In the formula (IV), $R^{401}$ to $R^{416}$ each independently represents a hydrogen atom or a substituent.

The compound represented by the formula (IV) in the invention is suitably used for organic electroluminescent devices. An organic electroluminescent device excellent in efficiency and running durability can be obtained using the compound represented by the formula (IV), for example, as a host material of fluorescence devices or a host material of phosphorescence devices or for a hole transport layer or an electron transport layer.

The following are specific examples of the compounds represented by the formulae (I) to (IV) in the invention but the invention is not limited thereto.

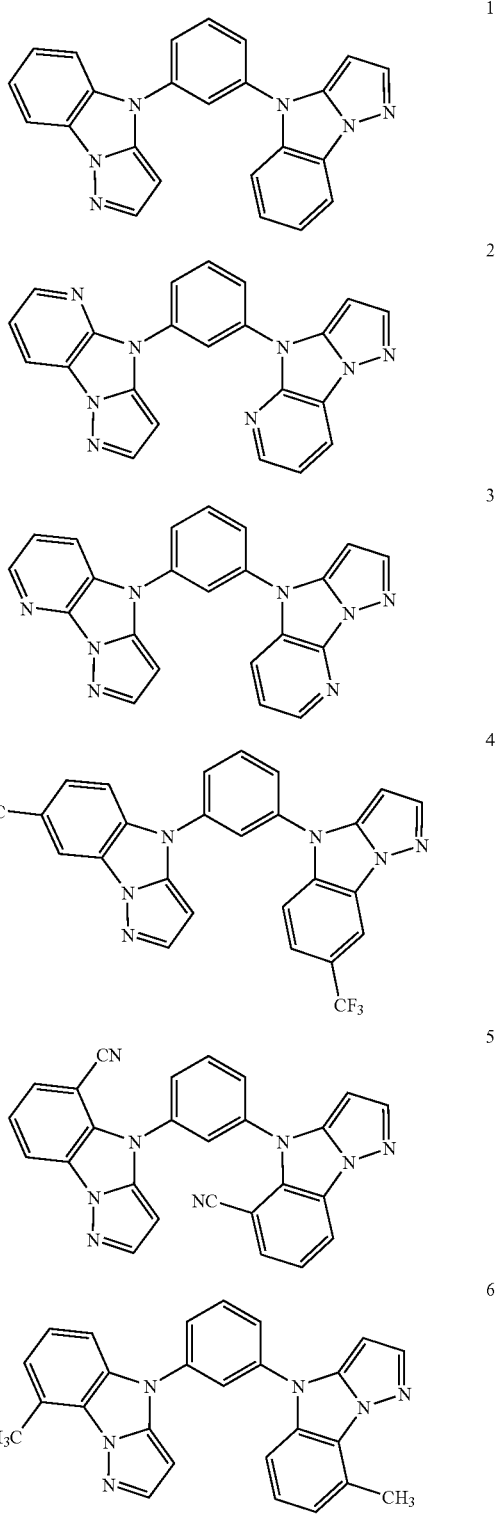

7
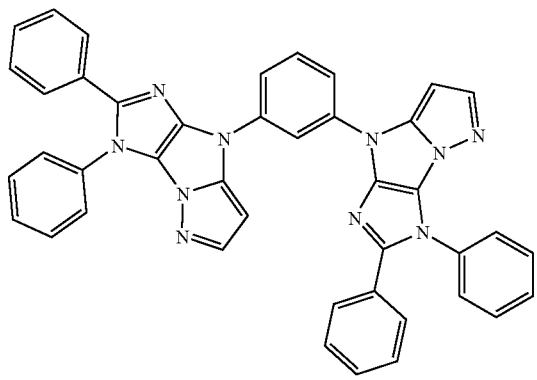
8
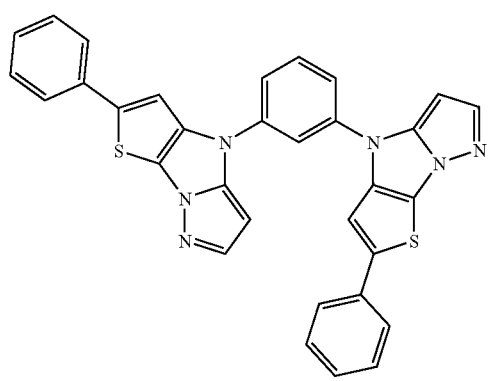
9
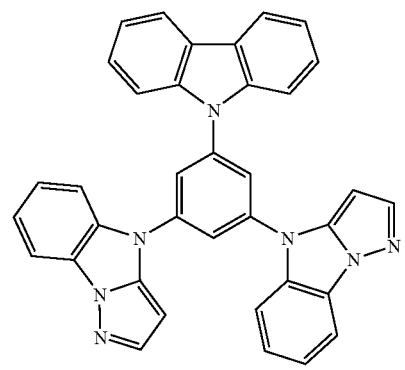
10
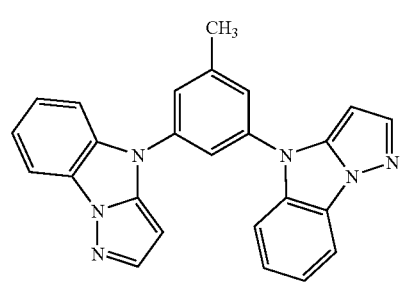
11
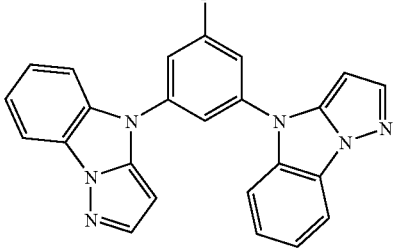
12
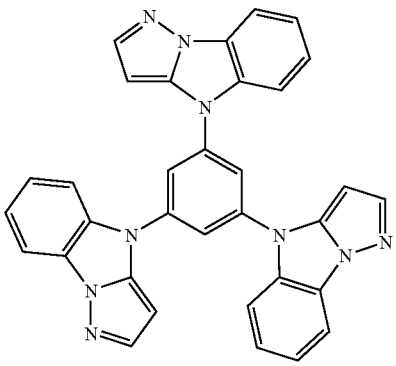
13
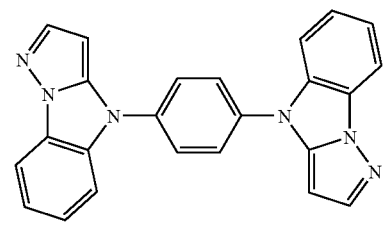
14
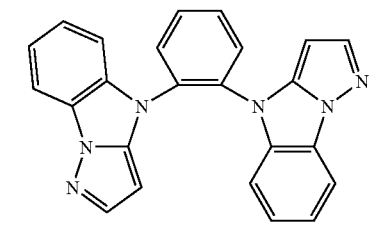
15
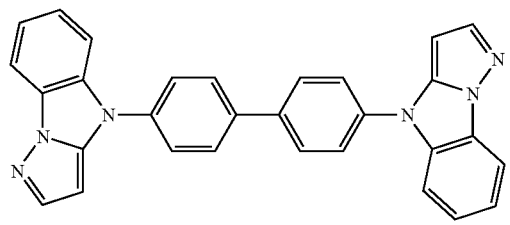
16
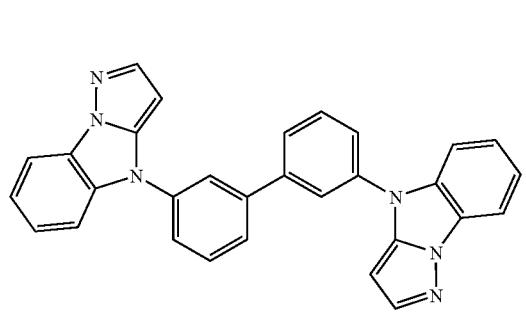

-continued

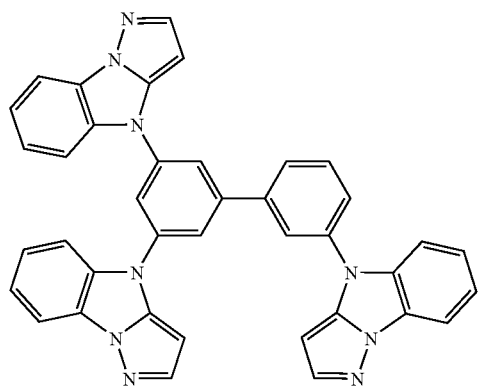
17

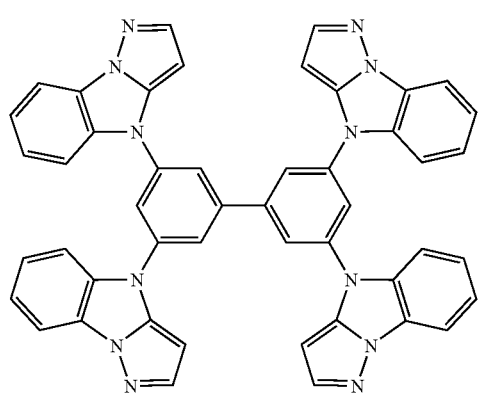
18

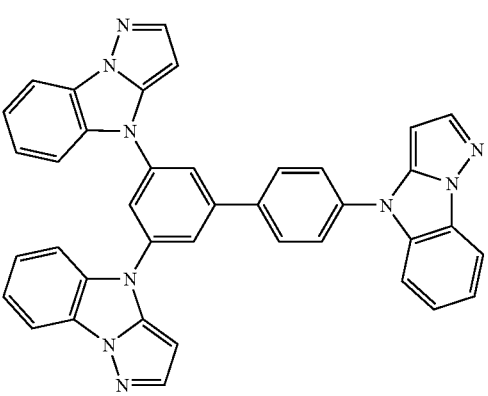
19

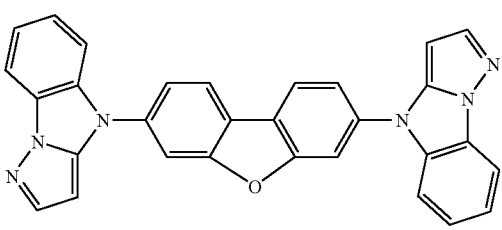
20

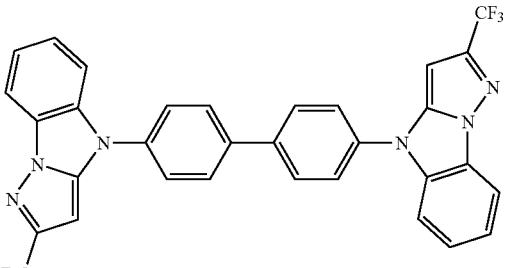
21

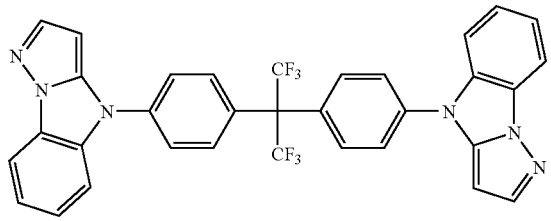
22

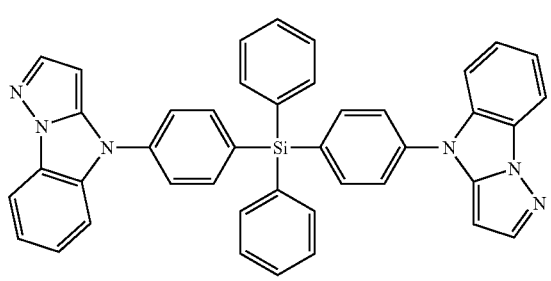
23

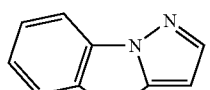

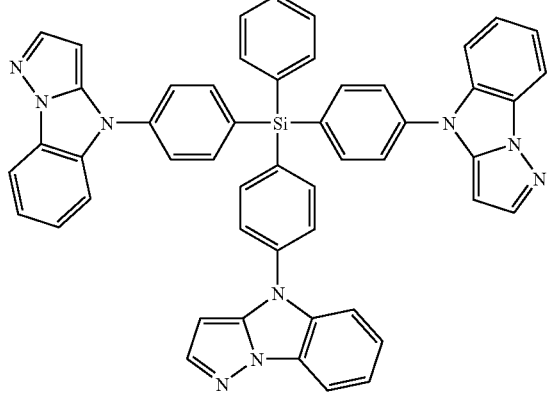
24

The compounds represented by the formulae (I) to (IV) in the invention can be synthesized by using various synthesis processes in combination. For example, a pyrazolobenzimidazole ring can be formed in accordance with the process described in *Heterocycles,* 16(7), 979-981 (1977) and *Monatshefte fur Chemie,* 114, 425-432 (1983). It is possible to achieve the synthesis either by coupling to a desired linking group in the presence of a Pd catalyst or Cu catalyst, followed by ring closure, or linking to a linking group after construction of a fused ring skeleton.

In consideration of durability of the device, the glass transition temperature (Tg) of the compound of the invention is preferably 80° C. or greater but not greater than 300° C., more preferably 100° C. or greater but not greater than 300° C., still more preferably 120° C. or greater but not greater than 300° C., still more preferably 130° C. or greater but not greater than 300° C., particularly preferably 150° C. or greater but not greater than 300° C.

Tg can be confirmed by thermal analysis such as differential scanning calorimetry (DSC) or differential thermal analysis (DTA), X-ray diffraction (XRD), or observation through a polarizing microscope.

When the device of the invention is a light emitting device making use of phosphorescence, the lowest excited triplet energy ($T_1$ energy) of the compound of the invention is preferably 60 kcal/mol (251.40 kJ/mol) or greater but not greater than 95 kcal/mol (398.05 kJ/mol), more preferably 65 kcal/mol (272.35 kJ/mol) or greater but not greater than 95 kcal/mol (398.05 kJ/mol), still more preferably 68 kcal/mol (284.92 kJ/mol) or greater but not greater than 95 kcal/mol (398.05 kJ/mol).

$T_1$ energy can be determined from the short-wavelength edge of the phosphorescence spectrum of a thin film of a material. For example, the material is formed into a film having a thickness of about 50 nm on a cleaned quartz glass substrate by vacuum deposition and the phosphorescence spectrum of the resulting thin film is measured using "Hitachi F-7000 Fluorescence Spectrophotometer" (trade name; product of Hitachi Hi-technologies) under a liquid nitrogen temperature. The $T_1$ energy can be determined by converting the rising wavelength on the short wavelength side of the resulting emission spectrum into an energy unit.

An organic electroluminescent device containing the compound of the invention will next be described.
(Organic Electroluminescent Device)

Detailed description on the constitution, substrate, cathode, and anode of an organic electroluminescent device can be found in, for example, JP-A-2008-270736 and embodiments in the description can be applied to the invention.
(Light Emitting Layer)
<Light Emitting Material>

Detailed description on light emitting materials (fluorescent material and phosphorescent material) can be found in JP-A-2008-270736 and embodiments in the description can be applied to the invention.

As the phosphorescent material, an iridium complex, platinum complex, or rhenium complex containing at least one coordination manner selected from a metal-carbon bond, a metal-nitrogen bond, a metal-oxygen bond, and a metal sulfur bond is preferred. Further, an iridium complex, platinum complex, or rhenium complex containing a tridentate or higher multidentate ligand is particularly preferred from the standpoint of luminous efficiency, running durability, chromaticity, and the like. A platinum complex having a tridentate or tetradentate ligand is most preferred.

The platinum complex is preferably represented by the following formula (C-1).

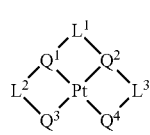

(C-1)

In the formula (C-1), $Q^1$, $Q^2$, $Q^3$ and $Q^4$ each independently represents a ligand coordinated to Pt and $L^1$, $L^2$ and $L^3$ each independently represents a single bond or a divalent linking group.

The formula (C-1) will be explained below. $Q^1$, $Q^2$, $Q^3$, and $Q^4$ each independently represents a ligand coordinated to Pt. At this time bonds of $Q^1$, $Q^2$, $Q^3$, and $Q^4$ to Pt each may be any of a covalent bond, an ionic bond, and a coordinate bond. The atoms bound to Pt in $Q^1$, $Q^2$, $Q^3$, and $Q^4$ are preferably a carbon atom, a nitrogen atom, an oxygen atom, a sulfur atom, or a phosphorus atom. It is preferred that at least one of the atoms bound to Pt in $Q^1$, $Q^2$, $Q^3$ and $Q^4$ is a carbon atom; and more preferred that two of them are carbon atoms.

$Q^1$, $Q^2$, $Q^3$, and $Q^4$ bound to Pt via the carbon atom may be either an anionic ligand or a neutral ligand. Examples of the anionic ligand include a vinyl ligand, aromatic hydrocarbon ring ligands (such as benzene ligand, naphthalene ligand, anthracene ligand, and phenanthrene ligand), heterocyclic ligands (such as furan ligand, thiophene ligand, pyridine ligand, pyrazine ligand, pyrimidine ligand, pyridazine ligand, triazine ligand, thiazole ligand, oxazole ligand, pyrrole ligand, imidazole ligand, pyrazole ligand, and triazole ligand, and fused ring products containing these ligands (such as quinoline ligand and benzothiazole ligand)). Examples of the neutral ligand include a carbene ligand.

$Q^1$, $Q^2$, $Q^3$, and $Q^4$ bound to Pt via the nitrogen atom may be either a neutral ligand or an anionic ligand. Examples of the neutral ligand include nitrogen-containing aromatic heterocyclic ligands (such as pyridine ligand, pyrazine ligand, pyrimidine ligand, pyridazine ligand, triazine ligand, imidazole ligand, pyrazole ligand, triazole ligand, oxazole ligand, and thiazole ligand, and fused ring products containing these ligands (e.g., quinoline ligand and benzimidazole ligand)), an amine ligand, a nitrile ligand, and an imine ligand. Examples of the anionic ligand include an amino ligand, an imino ligand, and nitrogen-containing aromatic heterocyclic ligands (such as pyrrole ligand, imidazole ligand, and triazole ligand, and fused ring products containing these ligands (e.g., indole ligand and benzimidazole ligand)).

$Q^1$, $Q^2$, $Q^3$ and $Q^4$ bound to Pt via the oxygen atom may be either a neutral ligand or an anionic ligand. Examples of the neutral ligand include an ether ligand, a ketone ligand, an ester ligand, an amide ligand, and oxygen-containing heterocyclic ligands (such as furan ligand and oxazole ligand, and fused ring products containing these ligands (e.g., benzoxazole ligand)). Examples of the anionic ligand include an alkoxy ligand, an aryloxy ligand, a heteroaryloxy ligand, an acyloxy ligand, and a silyloxy ligand.

$Q^1$, $Q^2$, $Q^3$ and $Q^4$ bound to Pt via the sulfur atom may be either a neutral ligand or an anionic ligand. Examples of the neutral ligand include a thioether ligand, a thioketone ligand, a thioester ligand, a thioamide ligand, and sulfur-containing heterocyclic ligands (such as thiophene ligand and thiazole ligand, and fused ring products containing these ligands (e.g., benzothiazole ligand)). Examples of the anionic ligand include an alkylmercapto ligand, an arylmercapto ligand, and a hetero-arylmercapto ligand.

$Q^1$, $Q^2$, $Q^3$ and $Q^4$ bound to Pt via the phosphorus atom may be either a neutral ligand or an anionic ligand. Examples of the neutral ligand include a phosphine ligand, a phosphate ester ligand, a phosphite ester ligand, and phosphorus-containing heterocyclic ligands (such as phosphinine ligand). Examples of the anionic ligand include a phosphino ligand, a phosphinyl ligand, and a phosphoryl ligand.

Each of the groups represented by $Q^1$, $Q^2$, $Q^3$, and $Q^4$ may have a substituent, and as the substituent, those exemplified above in Substituent group A can be used as needed. Substituents may be linked to each other ($Q^3$ and $Q^4$ may be linked to each other to form a Pt complex with a cyclic tetradentate ligand).

The groups represented by $Q^1$, $Q^2$, $Q^3$ and $Q^4$ are preferably an aromatic hydrocarbon ring ligand bound to Pt via the carbon atom, an aromatic heterocyclic ligand bound to Pt via the carbon atom, a nitrogen-containing aromatic heterocyclic ligand bound to Pt via the nitrogen atom, an acyloxy ligand, an alkyloxy ligand, an aryloxy ligand, a heteroaryloxy ligand, and a silyloxy ligand, more preferably an aromatic hydrocarbon ring ligand bound to Pt via the carbon atom, an aromatic heterocyclic ligand bound to Pt via the carbon atom, a nitrogen-containing aromatic heterocyclic ligand bound to Pt via the nitrogen atom, an acyloxy ligand, and an aryloxy ligand; still more preferably an aromatic hydrocarbon ring ligand bound to Pt via the carbon atom, an aromatic heterocyclic ligand bound to Pt via the carbon atom, a nitrogen-containing aromatic heterocyclic ligand bound to Pt via the nitrogen atom, and an acyloxy ligand.

$L^1$, $L^2$ and $L^3$ each represents a single bond or a divalent linking group. Examples of the divalent linking group represented by $L^1$, $L^2$ and $L^3$ include alkylene groups (such as methylene, ethylene, and propylene), arylene groups (such as phenylene and naphthalenediyl), heteroarylene groups (such as pyridinediyl and thiophenediyl), imino groups (—NR—) (such as phenylimino), an oxy group (—O—), a thio group (—S—), phosphinidene groups (—PR—) (such as phenylphosphinidene), and sibylline groups (—SiRR'—) (such as dimethylsilylene and diphenylsilylene), and combinations of these groups. These linking groups may have a substituent further.

Each of $L^1$, $L^2$ and $L^3$ preferably represents a single bond, an alkylene group, an arylene group, a heteroarylene group, an imino group, an oxy group, a thio group, or a sibylline group, more preferably a single bond, an alkylene group, an arylene group, or an imino group, still more preferably a single bond, an alkylene group, or an arylene group, still more preferably a single bond, a methylene group, or a phenylene group, still more preferably a single bond, a di-substituted methylene group, still more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, particularly preferably a single bond, a dimethylmethylene group, a diphenylmethylene group, or a cyclohexanediyl group.

The platinum complex represented by formula (C-1) is more preferably represented by the following formula (C-2).

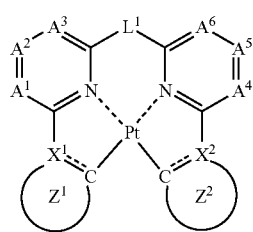

(C-2)

In the formula (C-2), $L^1$ represents a single bond or a divalent linking group; $Q^1$ to $Q^6$ each independently represents C—R or N; R represents a hydrogen atom or a substituent; $Q^1$ and $Q^2$ each independently represents C or N; and $Z^1$ and $Z^2$ each independently represents a 5- or 6-membered aromatic ring or aromatic heterocycle formed together with X—C in the formula.

Formula (C-2) will next be described. $L^1$ has the same meaning as that in the formula (C-1) and the preferred range of it is also the same. $Q^1$ to $Q^6$ each independently represents C—R or N and R represents a hydrogen atom or a substituent. As the substituent represented by R, those exemplified above in Substituent group A can be used.

$Q^1$ to $Q^6$ each preferably represents C—R, and Rs may be linked to each other to form a ring. When $Q^1$ to $Q^6$ represent C—R, R represented by $Q^2$ and $Q^5$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, particularly preferably a hydrogen atom or a fluorine group. On the other hand, R represented by $Q^1$, $Q^3$, $Q^4$, and $Q^6$ is preferably a hydrogen atom, an alkyl group, an aryl group, an amino group, an alkoxy group, an aryloxy group, a fluorine group, or a cyano group, more preferably a hydrogen atom, an amino group, an alkoxy group, an aryloxy group, or a fluorine group, particularly preferably a hydrogen atom. $Q^1$ and $Q^2$ each represents C or N. $Z^1$ represents a 5- or 6-membered aromatic hydrocarbon ring or aromatic heterocyclic ring formed together with $Q^1$—C in the formula. $Z^2$ represents a 5- or 6-membered aromatic hydrocarbon ring or aromatic heterocycle formed together with $Q^2$—C in the formula. Examples of the aromatic hydrocarbon ring or aromatic heterocycle represented by $Z^1$ and $Z^2$ include a benzene ring, a naphthalene ring, an anthracene ring, a pyrene ring, a phenanthrene ring, a perylene ring, a pyridine ring, a quinoline ring, an isoquinoline ring, a phenanthridine ring, a pyrimidine ring, a pyrazine ring, a pyridazine ring, a triazine ring, a cinnoline ring, an acridine ring, a phthalazine ring, a quinazoline ring, a quinoxaline ring, a naphthyridine ring, a pteridine ring, a pyrrole ring, a pyrazole ring, a triazole ring, an indole ring, a carbazole ring, an indazole ring, a benzimidazole ring, an oxazole ring, a thiazole ring, an oxadiazole ring, a thiadiazole ring, a benzoxazole ring, a benzothiazole ring, an imidazopyridine ring, a thiophene ring, a benzothiophene ring, a furan ring, a benzofuran ring, a phosphor ring, a phosphinine ring, and a silole ring. $Z^1$ and $Z^2$ may have a substituent, and as the substituent, those exemplified above in Substituent group A can be used. Further, $Z^1$ and $Z^2$ may form a fused ring with another ring.

$Z^1$ and $Z^2$ each preferably represents a benzene ring, a naphthalene ring, a pyrazole ring, an imidazole ring, a triazole ring, a pyridine ring, an indole ring, or a thiophene ring, more preferably a benzene ring, a pyrazole ring, or a pyridine ring.

The platinum complex represented by formula (C-2) is more preferably represented by the following formula (C-3).

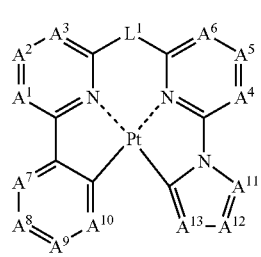

(C-3)

In the formula (C-3), $Q^1$ to $Q^{13}$ each independently represents C—R or N, R represents a hydrogen atom or a substituent, and $L^1$ represents a single bond or a divalent linking group.

The formula (C-3) will next be described. $L^1$ and $Q^1$ to $Q^6$ have the same meanings as those of the formula (C-2) and the preferred ranges of them are also the same. $Q^7$, $Q^8$, $Q^9$, and $Q^{10}$ each independently represents C—R or N and preferably, at least one of $Q^7$, $Q^8$, $Q^9$, and $Q^{10}$ represents N. R represents a hydrogen atom or a substituent. As the substituent represented by R, those exemplified in Substituent group A can be used. When $Q^7$, $Q^8$, $Q^9$, and $Q^{10}$ represent C—R, R is preferably a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably an alkyl group, a perfluoroalkyl group, an aryl group, a dialkylamino group, a cyano group, or a fluorine atom, still more preferably an alkyl group, a trifluoromethyl group, or a fluorine atom. If possible, substituents may be linked to each other to form a fused ring structure.

Preferably, at least one of $Q^7$, $Q^8$, $Q^9$, and $Q^{10}$ represents an N atom. The number of N atoms is preferably 1 or 2, more preferably 1.

Any of $Q^7$, $Q^8$, $Q^9$, and $Q^{10}$ may be an N atom. It is preferred that $Q^8$ or $Q^9$ represents an N atom; more preferred that $Q^8$ represents an N atom.

Examples of the 6-membered ring formed of two carbon atoms and $Q^7$, $Q^8$, $Q^9$, and $Q^{10}$ include a benzene ring, a pyridine ring, a pyrazine ring, a pyrimidine ring, a pyridazine ring, and a triazine ring, more preferably a benzene ring, a pyridine ring, a pyrazine ring, a pyrimidine ring, or a pyridazine ring, particularly preferably a pyridine ring.

$Q^{11}$, $Q^{12}$, and $Q^{13}$ each independently represents C—R or N. R represents a hydrogen atom or a substituent. As the substituent represented by R, those exemplified above in Substituent group A can be used. When $Q^{11}$, $Q^{12}$, and $Q^{13}$ each represents C—R, R is preferably a hydrogen atom, an alkyl group, a perfluoroalkyl group, an aryl group, an aromatic heterocyclic group, a dialkylamino group, a diarylamino group, an alkyloxy group, a cyano group, or a halogen atom, more preferably an alkyl group, a perfluoroalkyl group, an aryl group, a dialkylamino group, a cyano group, or a fluorine atom, still more preferably an alkyl group, a trifluoromethyl group, or a fluorine atom. If possible, the substituents may be linked to each other to form a fused ring structure.

The platinum complex represented by the formula (C-2) is more preferably represented by the following formula (C-4):

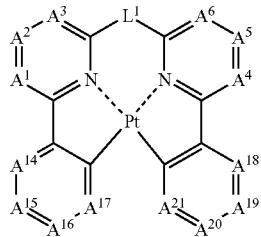

Formula (C-4)

In the formula (C-4), $Q^1$ to $Q^6$ and $Q^{14}$ to $Q^{21}$ each independently represents C—R or N, R represents a hydrogen atom or a substituent, and $L^1$ represents a single bond or a divalent linking group.

The formula (C-4) will next be described.

$Q^1$ to $Q^6$ and $Q^{14}$ to $Q^{17}$ each independently represents C—R or N. R represents a hydrogen atom or a substituent. $Q^1$ to $Q^6$ and $L^1$ have the same meanings as $Q^1$ to $Q^6$ and $L^1$ in the formula (C-2) and preferred ranges of them are also the same.

As $Q^{14}$ to $Q^{21}$, the number of N (nitrogen atoms) in $Q^{14}$ to $Q^{17}$ and $Q^{18}$ to $Q^{21}$ is preferably from 0 to 2, more preferably from 0 to 1, respectively. N is selected preferably from $Q^{15}$ to $Q^{17}$ and $Q^{19}$ to $Q^{21}$, more preferably from $Q^{15}$, $Q^{16}$, $Q^{19}$, and $Q^{20}$, particularly preferably from $Q^{15}$ and $Q^{19}$.

When $Q^{14}$ to $Q^{21}$ represents C—R, R of $Q^{15}$ or $Q^{19}$ is preferably a hydrogen atom, an alkyl group, a polyfluoroalkyl group, an aryl group, an amino group, an alkoxy group, an aryloxy group, a fluorine group, or a cyano group; more preferably a hydrogen atom, a polyfluoroalkyl group, an alkyl group, an aryl group, a fluorine group, or a cyano group; particularly preferably a hydrogen atom, a polyfluoroalkyl group, or a cyano group.

R represented by $Q^{14}$, $Q^{16}$, $Q^{18}$, or $Q^{20}$ is preferably a hydrogen atom, an alkyl group, a polyfluoroalkyl group, an aryl group, an amino group, an alkoxy group, an aryloxy group, a fluorine group, or a cyano group; more preferably a hydrogen atom, a polyfluoroalkyl group, a fluorine group, or a cyano group; particularly preferably a hydrogen atom or a fluorine group.

R represented by $Q^{17}$ or $Q^{21}$ is preferably a hydrogen atom or a fluorine group, more preferably a hydrogen atom. When any of $Q^{14}$ to $Q^{16}$ and $Q^{18}$ to $Q^{20}$ represents C—R, Rs may be coupled to each other to form a ring.

Specific examples of the light emitting material include those described in the paragraphs from (0107) to (0108) of JP-A-2009-152571 (Japanese Patent Application No. 2008-298282) and those described in the paragraphs from (0109) to (0111) of JP-A-2009-283891 (Japanese Patent Application No. 2008-310220).

The light emitting material is generally contained in the light emitting layer in an amount of from 0.1 mass % to 50 mass % based on the total mass of the compounds constituting the light emitting layer. It is preferably from 1 mass % to 50 mass %, more preferably from 2 mass % to 40 mass % from the standpoint of durability and external quantum efficiency.

Although no particular limitation is imposed on the thickness of the light emitting layer, a thickness of from 2 nm to 500 nm is typically preferred. From the standpoint of external quantum efficiency, the thickness is more preferably from 3 nm to 200 nm, still more preferably from 5 nm to 100 nm.

<Host Material>

As the host material usable in the invention, the following materials as well as the compounds of the invention can be used.

Examples of the host materials include pyrrole; indole; carbazole; azaindole; azacarbazole; triazole; oxazole; oxadiazole; pyrazole; imidazole; thiophene; polyarylalkane; pyrazoline; pyrazolone; phenylenediamine; arylamine; amino-substituted chalcone; styrylanthracene; fluorenone; hydrazone; stilbene; silazane; aromatic tertiary amine compounds; styrylamine compounds; porphyrin compounds; conductive polymers or oligomers such as polysilane compounds, poly(N-vinylcarbazole), aniline copolymers, thiophene oligomers, and polythiophene; organic silanes; carbon films; tetracarboxylic anhydrides of hetercocyclic groups such as pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, and naphthaleneperylene; phthalocyanine; various metal complexes such as metal complexes of 8-quinolinol derivatives and metal complexes having metal phthalocyanine, benzoxazole, or benzothiazole as a ligand thereof; and derivatives thereof (which may have a substituent or a fused ring).

In the light emitting layer in the invention, the host material (including the compound represented by the formula (I)) has preferably a lowest excited triplet energy ($T_1$ energy) higher than the $T_1$ energy of the phosphorescent material from the standpoint of color purity, luminous efficiency, and running durability.

Although the content of the host compound in the invention is not particularly limited, it is preferably 15 mass % or greater but not greater than 95 mass % based on the total mass of the compounds constituting the light emitting layer from the standpoint of luminous efficiency and drive voltage.

—Hole Injection Layer, Hole Transport Layer—

The hole injection layer and hole transport layer are layers having a function of receiving holes from an anode or anode side and transporting them to a cathode side.

—Electron Injection Layer, Electron Transport Layer—

The electron injection layer and electron transport layer are layers having a function of receiving electrons from a cathode or a cathode side and transporting them to an anode side.

Embodiments on a hole injection layer, hole transport layer, electron injection layer, and electron transport layer, described in the paragraphs from (0165) to (0167) of JP-A-2008-270736, can be applied to the invention.

—Hole Blocking Layer—

The hole blocking layer has a function of preventing the holes transported from the anode side to the light emitting layer from passing through to the cathode side. In the invention, the hole blocking layer can be provided as an organic layer adjacent to the light-emitting layer on the cathode side.

Examples of organic compounds constituting the hole blocking layer include aluminum complexes such as aluminum (III) bis(2-methyl-8-quinolinato) 4-phenylphenolate (which will hereinafter be abbreviated as "BAlq"), triazole derivatives, and phenanthroline derivatives such as 2,9-dimethyl-4,7-diphenyl-1,10-phenanthroline (which will hereinafter be abbreviated as "BCP").

The thickness of the hole blocking layer is preferably from 1 nm to 500 nm, more preferably from 5 nm to 200 nm, still more preferably from 10 nm to 100 nm.

The hole blocking layer may have either a single layer structure composed of one or more materials selected from the above-exemplified materials or a multilayer structure composed of a plurality of layers having the same composition or different compositions.

<Protective Layer>

In the invention, the entirety of the organic EL device may be protected with a protective layer.

Embodiments on a protective layer, described in the paragraphs from (0169) to (0170) of JP-A-2008-270736, can be applied to the invention.

<Substrate>

As the substrate to be used in the invention, a substrate not causing scattering or attenuation of light emitted from the organic layer is preferred.

<Anode>

The anode may typically have a function as an electrode for supplying holes to the organic layer. No particular limitation is imposed on the shape, structure, size and the like of it. It may be selected as needed from known electrode materials, depending on the intended use or purpose of the light emitting device. As described above, the anode is typically provided as a transparent anode.

<Cathode>

The cathode may typically have a function as an electrode for injecting electrons to the organic layer. No particular limitation is imposed on the shape, structure, size, and the like of it. It may be selected as needed from known electrode materials, depending on the intended use or purpose of the light emitting device.

Embodiments on a substrate, anode, and cathode, described in the paragraphs from (0070) to (0089) of JP-A-2008-270736, can be applied to the invention.

<Sealing Container>

The entirety of the device of the invention may be sealed with a sealing container.

Embodiments on a sealing container, described in the paragraph (0171) of JP-A-2008-270736, can be applied to the invention.

(Driving)

Light emission of the organic electroluminescent device of the invention can be realized by applying DC (it may contain AC component, if necessary) voltage (typically, from 2 volts to 15 volts) or DC current between the anode and the cathode.

Embodiments on a driving method of an organic electroluminescent device, described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308, can be applied to the driving method in the invention.

The light emitting device of the invention can have improved light extraction efficiency by various known measures. It can have improved light extraction efficiency and therefore have improved external quantum efficiency by, for example, processing the surface shape of the substrate (for example, by forming minute concavo-convex patterns), by controlling the refractive indices of the substrate, ITO layer and organic layers, and by controlling the thicknesses of the substrate, ITO layer and organic layers.

The light emitting device of the invention may employ a so-called top emission system in which light is extracted from the anode side.

The organic EL device of the invention may have a charge generating layer between the light emitting layers in order to improve its luminous efficiency.

The charge generating layer has both a function of generating charges (holes and electrons) at the time of application of an electric field and a function of injecting the charges thus generated to the layer adjacent to the charge generating layer.

As the material constituting the charge generating layer, any material can be used insofar as it has the above functions, and the charge generating layer may be formed of a single compound or a plurality of compounds.

Described specifically, any of a material having conductivity, a material having semi-conductivity such as a doped organic layer, and a material having an electric insulating property is usable. Examples include those in JP-A-11-329748, JP-A-2003-272860, and JP-A-2004-39617.

More specifically, transparent conductive materials such as ITO and IZO (indium zinc oxide), fullerenes such as C60, conductive organic materials such as oligothiophene, conductive organic materials such as metal phthalocyanines, metal-free phthalocyanines, metal porphyrins, and metal-free porphyrins, metal materials such as Ca, Ag, Al, Mg:Ag alloy, Al:Li alloy, and Mg:Li alloy, hole conductive materials, and electron conductive materials, and mixtures of these materials may be used.

Examples of the hole-conductive materials include materials obtained by doping an oxidant having an electron withdrawing property such as F4-TCNQ, TCNQ, or $FeCl_3$ to a hole transporting organic material such as 2-TNATA or NPD, P-type conductive polymers, and P-type semiconductors. Examples of the electron conductive materials include materials obtained by doping a metal or a metal compound having a work function of less than 4.0 eV to an electron transporting organic material, N-type conductive polymers, and N-type semiconductors. Examples of the N-type semiconductors include N-type Si, N-type CdS, and N-type ZnS, while those of the P-type semiconductors include P-type Si, P-type CdTe, and P-type CuO.

Further, electrically insulating materials such as $V_2O_5$ can also be used as the charge generating layer.

The charge generating layer may be a monolayer or a stack of a plurality of layers. Examples of the stack of a plurality of layers include a structure obtained by stacking a material having conductivity such as transparent conduction material or metal material and a hole conductive material or an electron-conductive material and a structure obtained by stacking the hole conductive material and the electron-conductive material.

The thickness and materials of the charge generating layer are preferably selected so that the transmittance of visible light be 50% or greater. Although no particular limitation is imposed on the thickness, it is preferably from 0.5 nm to 200 nm, more preferably from 1 nm to 100 nm, still more preferably from 3 nm to 50 nm, particularly preferably from 5 nm to 30 nm.

The formation method of the charge generating layer is not particularly limited and the above-described formation method of the organic layers can be used.

The charge generating layer is formed between the above-described two or more light emitting layers and it may have, on the anode side and cathode side thereof, a material having a function of injecting charges to a layer adjacent to the charge generating layer. In order to enhance the electron injection property to a layer adjacent to the anode side of the charge generating layer, an electron injecting compound such as BaO, SrO, $Li_2O$, LiCl, LiF, $MgF_2$, MgO, or $CaF_2$ may be stacked on the anode side of the charge generating layer.

Besides, the material of the charge generating layer can be selected with reference to JP-A-2003-45676, and U.S. Pat. Nos. 6,337,492, 6,107,734, and 6,872,472.

The organic EL device in the invention may have a resonator structure. For example, the organic EL device has a structure obtained by superimposing, on a transparent substrate, a multilayer film mirror obtained by stacking a plurality of layers different in refractive index, a transparent or translucent electrode, a light emitting layer, and a metal electrode. The light generated in the light emitting layer repeats reflection and resonates between the multilayer film mirror and the metal electrode while using them as reflectors.

In another preferred mode, a transparent or translucent electrode and a metal electrode respectively function as reflectors on a transparent substrate and light generated in the light emitting layer repeats reflection and resonates between them.

In order to form a resonant structure, effective refractive indices of two reflectors and an optical path length determined by the refractive index and thickness of each layer between the reflectors are adjusted to be optimum values for achieving a desired resonance wavelength. The calculation formula in the case of the first mode is described in JP-A-9-180883, while that in the case of the second mode is described in JP-A-2004-127795.

(Intended Use of the Invention)

The organic electroluminescent device of the invention can be used suitably in display devices, displays, backlights, electrophotography, illumination light sources, recording light sources, exposure light sources, reading light sources, indicators, signboards, interior designs, optical communications, and the like.

As a method of obtaining a full color organic EL display, for example, as described in *Monthly Display*, September, 2000, pp. 33-37, known are a three color emission method in which organic EL devices emitting lights corresponding to primary three colors (blue (B), green (G), and red (R)), respectively, are arrayed on a substrate; a white color method in which white light emitted from a white luminescent organic EL device is separated into three primary colors through color filters; and a color conversion method in which blue light emitted from a blue luminescent organic EL device is converted into red (R) and green (G) through fluorescent color layers.

Further, by using, in combination, a plurality of organic EL devices different in an emission color and available by the above method, a flat panel light source having a desired emission color can be obtained. Examples of such a light source include a white color emitting light source using a blue light emitting device and a yellow light emitting device in combination and a white color emitting light source using a blue light emitting device, a green light emitting device, and a red light emitting device in combination.

EXAMPLES

The invention will be described in further detail by Examples. It should however be borne in mind that the invention is not limited to or by them.

Synthesis Example

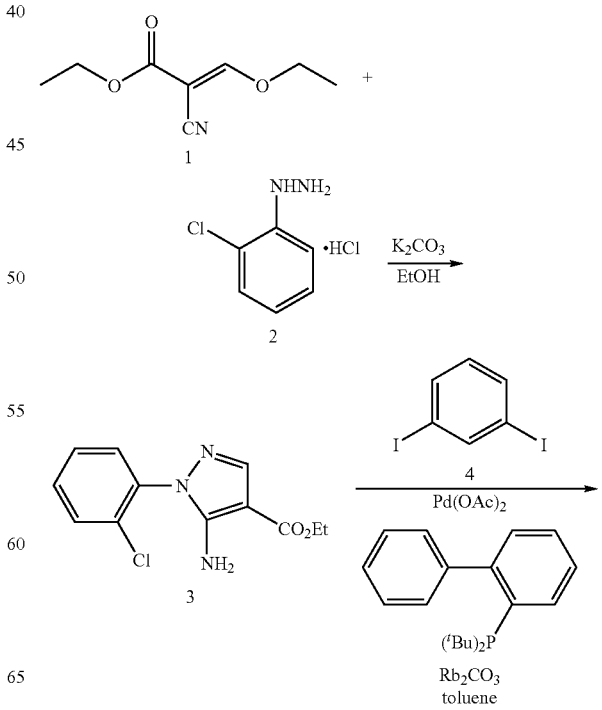

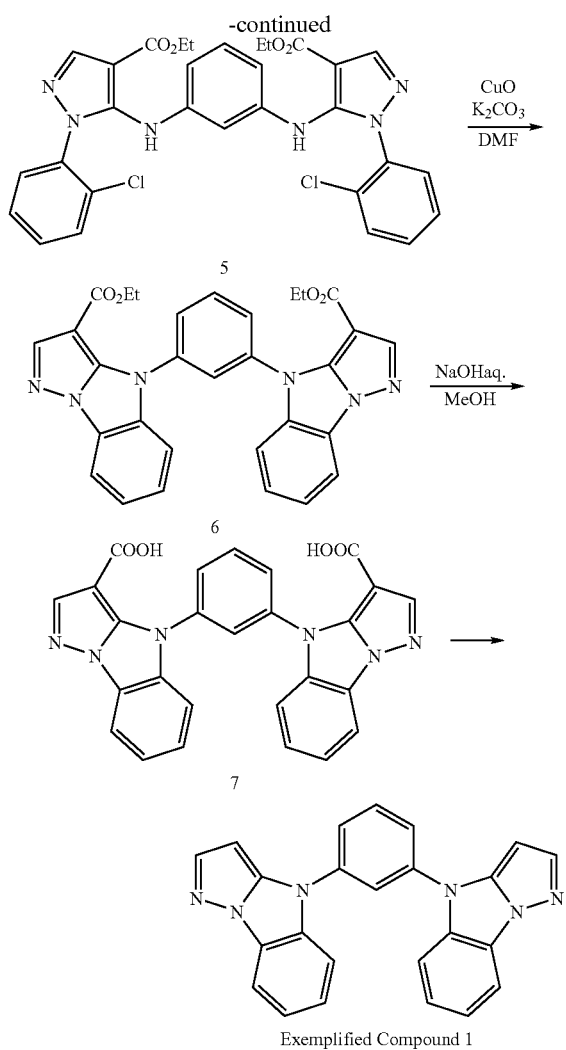

(Synthesis of Compound 3)

Compound 1 (50 g, 0.30 mol) and Compound 2 (52.6 g, 0.30 mol) were dissolved in 300 mL of ethanol in a nitrogen atmosphere. Potassium carbonate (45 g, 0.33 mol) was added to the resulting solution and the mixture was heated and refluxed for 18 hours. After cooling to room temperature, the solvent was distilled off under reduced pressure. The residue was purified by silica gel column chromatography (ethyl acetate) to yield 70.2 g (yield: 90%) of Compound 3.

(Synthesis of Compound 5)

Compound 3 (69 g, 0.26 mol) and Compound 4 (43 g, 0.13 mol) were dissolved in 800 mL of toluene in a nitrogen atmosphere. Then, 2-(d-t-butylphosphino)biphenyl (12 g, 0.04 mol), rubidium carbonate (120 g, 0.52 mol), and palladium acetate (2.9 g, 0.01 mol) were added to the resulting solution and the resulting mixture was heated and refluxed for 5 hours. After cooling to room temperature, the reaction mixture was extracted with ethyl acetate/water. The organic layer was washed successively with water and saturated saline and dried over magnesium sulfate. The solvent was distilled off and the residue was purified by silica gel column chromatography (hexane:ethyl acetate=3:1) to yield 60 g (yield: 76%) of Compound 5.

(Synthesis of Compound 6)

Compound 5 (60 g, 0.1 mol), cupric oxide (1.6 g, 0.02 mol), and potassium carbonate (28 g, 0.2 mol) were added to N,N-dimethylformamide. The resulting mixture was heated and refluxed for 10 hours. After cooling to 40° C., hot filtration was performed. The filtrate was extracted with ethyl acetate/water. The organic layer was washed successively with water and saturated saline and then, dried over magnesium sulfate. The solvent was distilled off. The solid thus obtained was recrystallized from ethyl acetate to yield 16 g (yield: 30%) of Compound 6.

(Synthesis of Compound 7)

Compound 6 (16 g, 30 mmol), a 2N NaOH aqueous solution (100 mL), and methanol (100 mL) were mixed and the resulting mixture was heated and refluxed for one hour. After cooling to room temperature, the reaction mixture was poured into water and neutralized with dilute hydrochloric acid to precipitate a colorless solid. The solid collected by filtration was washed with a small amount of methanol and dried to yield 12.5 g (yield: 88%) of Compound 7.

(Synthesis of Exemplified Compound 1)

Compound 7 (12.5 g, 0.26 mol) was charged in a flask and heated to 200° C. with an oil bath. The reaction was terminated after one hour heating. The solid thus obtained was washed with methanol to yield 10.0 g (yield: 98%) of Exemplified compound 1.

<Preparation of Comparative Device A-1>

An anode substrate obtained by forming a 150-nm thick ITO film on a glass substrate was washed. NPD was then deposited on the resulting anode substrate to give a film thickness of 40 nm. Then, XIX-5 and Pt1 were deposited at a mass ratio of 90:10 to give a film thickness of 30 nm, followed by deposition of BAlq thereon to give a film thickness of 30 nm. A patterned mask was placed on the resulting organic thin film and lithium fluoride was deposited as a cathode to give a film thickness of 1 nm. Then, aluminum was deposited thereon to give a film thickness of 100 nm to yield Comparative device A-1.

<Preparation of Devices of Examples A to L>

In a similar manner to that employed for the preparation of Comparative device A-1 except that XIX-5 was replaced with Exemplified compound 1, Invention device A-1 was prepared. Similarly, in a similar manner to that employed for the preparation of Comparative device A-1 except that the constitution of Comparative device A-1 was changed to that shown in Tables 1 to 5, devices of Examples A to L were prepared. The numeral in parentheses in the column of device constitution in these tables means film thickness (nm). The term "90% 1+10% Pt1(30)" in the table means that Exemplified compound 1 and Pt1 are used at a mass ratio of 90:10 to give a film thickness of 30 nm.

(Evaluation of Performance of Organic Electroluminescent Device)

(a) External Quantum Efficiency

A DC voltage was applied to each device by using "Source Measure Unit 2400" (trade name; product of Toyo Technica) to make each device emit light. The luminance was measured using "Luminance meter BM-8" (trade name; product of Topcon). Light emission spectrum and light emission wavelength were measured using "Spectrum Analyzer PMA-11" (trade name; product of Hamamatsu Photonics). Based on the measurement data thus obtained, external quantum efficiency at a luminance of approximately 100 cd/m$^2$ was calculated using the luminance conversion method.

(b) Running Durability

DC voltage was applied to each device to give a luminance of 1000 cd/m$^2$ and time necessary for the luminance to be reduced to 500 cd/m$^2$ was measured. The time necessary for the luminance to be reduced by half was used as an indicator for evaluation of running durability and the running durability was indicated as a relative value to that of Comparative device A-5 set at 10.

TABLE 1

| | Device No. | Device constitution | External quantum efficiency | Running durability |
|---|---|---|---|---|
| Example A (as host material of phosphorescence device) | Comparative device A-1 | ITO/NPD(40)/90% XIX-5 + 10% Pt1(30)/BAlq(30)/LiF/Al | 0.4% | 0 |
| | Comparative device A-2 | ITO/NPD(40)/90% XIX-9 + 10% Pt1(30)/BAlq(30)/LiF/Al | No light emission | Unmeasurable |
| | Comparative device A-3 | ITO/NPD(40)/90% XIX-11 + 10% Pt1(30)/BAlq(30)/LiF/Al | No light emission | Unmeasurable |
| | Comparative device A-4 | ITO/NPD(40)/90% HT-13 + 10% Pt1(30)/BAlq(30)/LiF/Al | No light emission | Unmeasurable |
| | Comparative device A-5 | ITO/NPD(40)/90% CBP + 10% Pt1(30)/BAlq(30)/LiF/Al | 0.8% | 10 |
| | Invention device A-1 | ITO/NPD(40)/90% 1 + 10% Pt1(30)/BAlq(30)LiF/Al | 7.5% | 100 |
| | Invention device A-2 | ITO/NPD(40)/90% 16 + 10% Pt1(30)/BAlq(30)/LiF/Al | 8.1% | 94 |
| | Invention device A-3 | ITO/NPD(40)/90% 23 + 10% Pt1(30)/BAlq(30)/LiF/Al | 7.4% | 80 |
| | Invention device A-4 | ITO/NPD(40)/90% 9 + 10% Pt1(30)/Balq(30)/LiF/Al | 8.4% | 130 |
| | Invention device A-5 | ITO/NPD(40)/90% 21 + 10% Pt1(30)/BAlq(30)/LiF/Al | 7.1% | 71 |
| | Invention device A-6 | ITO/NPD(40)/90% 18 + 10% Pt1(30)/BAlq(30)/LiF/Al | 6.9% | 75 |
| Example B (as host material of phosphorescence device) | Comparative device B-1 | ITO/NPD(40)/90% XIX-9 + 10% Pt2(30)/BAlq(30)/LiF/Al | No light emission | Unmeasurable |
| | Comparative device B-2 | ITO/NPD(40)/90% XIX-11 + 10% Pt2(30)/BAlq(30)/LiF/Al | No light emission | Unmeasurable |
| | Comparative device B-3 | ITO/NPD(40)/90% HT-13 + 10% Pt2(30)/BAlq(30)/LiF/Al | No light emission | Unmeasurable |
| | Invention device B-1 | ITO/NPD(40)/90% 1 + 10% Pt2(30)/Balq(30)/LiF/Al | 7.7% | 80 |
| | Invention device B-2 | ITO/NPD(40)/90% 9 + 10% Pt2(30)/Balq(30)/LiF/Al | 7.9% | 76 |
| | Invention device B-3 | ITO/NPD(40)/90% 23 + 10% Pt2(30)/BAlq(30)/LiF/Al | 7.1% | 83 |

TABLE 2

| | Device No. | Device constitution | External quantum efficiency | Running durability |
|---|---|---|---|---|
| Example C (as host material of phosphorrescence device) | Comparative device C-1 | ITO/NPD(50)/90% XIX-9 + 10% Pt3(30)/BAlq(30)/LiF/Al | No light emission | Unmeasurable |
| | Comparative device C-2 | ITO/NPD(50)/90% XIX-11 + 10% Pt3(30)/BAlq(30)/LiF/Al | No light emission | Unmeasurable |
| | Comparative device C-3 | ITO/NPD(50)/90% HT-13 + 10% Pt3(30)/BAlq(30)/LiF/Al | No light emission | Unmeasurable |
| | Comparative device C-4 | ITO/NPD(50)/90% HT-7 + 10% Pt3(30)/BAlq(30)/LiF/Al | 8.9% | 7 |
| | Invention device C-1 | ITO/NPD(50)/90% 1 + 10% Pt3(30)/Balq(30)/LiF/Al | 13.1% | 310 |
| | Invention device C-2 | ITO/NPD(50)/90% 16 + 10% Pt3(30)/BAlq(30)/LiF/Al | 14.0% | 290 |
| | Invention device C-3 | ITO/NPD(50)/90% 9 + 10% Pt3(30)/BAlq(30)/LiF/Al | 13.7% | 300 |
| Example D (as host material of phoshorescence device) | Comparative Device D-1 | ITO/NPD(40)/90% XIX-9 + 10% Flrpic(30)/BAlq(30)/LiF/Al | No light emission | Unmeasurable |
| | Comparative device D-2 | ITO/NPD(40)/90% XIX-11 + 10% Flrpic(30)/BAlq(30)/LiF/Al | No light emission | Unmeasurable |
| | Comparative device D-3 | ITO/NPD(40)/90% HT-7 + 10% Flrpic(30)/BAlq(30)/LiF/Al | 3.4% | 5 |
| | Invention device D-1 | ITO/NPD(40)/90% 1 + 10% Flrpic(30)/BAlq(30)/LiF/Al | 6.3% | 40 |
| | Invention device D-2 | ITO/NPD(40)/90% 18 + 10% Flrpic(30)/BAlq(30)/LiF/Al | 6.5% | 39 |
| | Invention device D-3 | ITO/NPD(40)/90% 21 + 10% Flrpic(30)/BAlq(30)/LiF/Al | 6.7% | 35 |

TABLE 3

| | Device No. | Device constitution | External quantum efficiency | Running durability |
|---|---|---|---|---|
| Example E (as host material of phosphorescence device) | Comparative device E-1 | ITO/NPD(50)/90% XIX-5 + 10% Irppy(30)/BAlq(30)/LiF/Al | 0.5% | 0 |
| | Comparative device E-2 | ITO/NPD(50)/90% XIX-9 + 10% Irppy(30)/BAlq(30)/LiF/Al | No light emission | Unmeasurable |
| | Comparative device E-3 | ITO/NPD(50)/90% HT-13 + 10% Irppy(30)/BAlq(30)/LiF/Al | No light emission | Unmeasurable |
| | Invention device E-1 | ITO/NPD(50)/90% 1 + 10% Irppy(30)/BAlq(30)/LiF/Al | 9.5% | 150 |
| | Invention device E-2 | ITO/NPD(50)/90% 16 + 10% Irppy(30)/BAlq(30)/LiF/Al | 8.2% | 145 |
| | Invention device E-3 | ITO/NPD(50)/90% 9 + 10% Irppy(30)/BAlq(30)/LiF/Al | 7.9% | 120 |
| Example F (as host material of phosphorescence device) | Comparative Device F-1 | ITO/NPD(50)/90% XIX-9 + 10% Ir(piq)$_3$ (30)/BAlq(30)/LiF/Al | No light emission | Unmeasurable |
| | Comparative device F-2 | ITO/NPD(50)/90% XIX-11 + 10% Ir(piq)$_3$ (30)/BAlq(30)/LiF/Al | No light emission | Unmeasurable |
| | Comparative device F-3 | ITO/NPD(50)/90% HT-13 + 10% Ir(piq)$_3$ (30)/BAlq(30)/LiF/Al | 2.9% | 80 |
| | Invention device F-1 | ITO/NPD(50)/90% 9 + 10% Ir(piq)$_3$(30)/BAlq(30)/LiF/Al | 5.2% | 110 |
| | Invention device F-2 | ITO/NPD(50)/90% 15 + 10% Ir(piq)$_3$(30)/BAlq(30)/LiF/Al | 6.3% | 210 |
| | Invention device F-3 | ITO/NPD(50)/90% 18 + 10% Ir(piq)$_3$(30)/BAlq(30)/LiF/Al | 6.3% | 220 |

TABLE 4

| | Device No. | Device constitution | External quantum efficiency | Running durability |
|---|---|---|---|---|
| Example G (as host material of phosphorescence device) | Comparative device G-1 | ITO/NPD(50)/90% XIX-9 + 10% Irpq2(acac) (30)/BAlq(30)/LiF/Al | No light emission | Unmeasurable |
| | Comparative device G-2 | ITO/NPD(50)/90% XIX-11 + 10% Irpq2(acac) (30)/BAlq(30)/LiF/Al | No light emission | Unmeasurable |
| | Comparative device G-3 | ITO/NPD(50)/90% HT-13 + 10% Irpq2(acac) (30)/BAlq(30)/LiF/Al | 3.2% | 70 |
| | Invention device G-1 | ITO/NPD(50)/90% 1 + 10% Irpq2(acac)(30)/BAlq(30)/LiF/Al | 5.4% | 140 |
| | Invention device G-2 | ITO/NPD(50)/90% 17 + 10% Irpq2(acac)(30)/BAlq(30)/LiF/Al | 7.5% | 200 |
| | Invention device G-3 | ITO/NPD(50)/90% 18 + 10% Irpq2(acac)(30)/BAlq(30)/LiF/Al | 6.1% | 240 |
| Example H (as host material of fluorescence device) | Comparative Device H-1 | ITO/NPD(50)/99% XIX-9 + 1% Coumarine 6(30)/BAlq(30)/LiF/Al | No light emission | Unmeasurable |
| | Comparative device H-2 | ITO/NPD(50)/99% HT-7 + 1% Coumarine 6(30)/BAlq(30)/LiF/Al | 1.1% | 6 |
| | Invention device H-1 | ITO/NPD(50)/99% 1 + 1% Coumarine6(30)/BAlq(30)/LiF/Al | 2.1% | 390 |
| | Invention device H-2 | ITO/NPD(50)/99% 16 + 1% Coumarine6(30)/BAlq(30)/LiF/Al | 2.4% | 320 |
| | Invention device H-3 | ITO/NPD(50)/99% 23 + 1% Coumarine6(30)/BAlq(30)/LiF/Al | 2.8% | 190 |
| Example I (as host material of fluorescence device) | Comparative Device I-1 | ITO/NPD(50)/99% XIX-9 + 1% rubrene(30)/BAlq(30)/LiF/Al | No light emission | Unmeasurable |
| | Comparative device I-2 | ITO/NPD(50)/99% HT-7 + 1% rubrene(30)/BAlq(30)/LiF/Al | 1.4% | 15 |
| | Invention device I-1 | ITO/NPD(50)/99% 1 + 1% rubrene(30)/BAlq(30)/LiF/Al | 2.2% | 330 |
| | Invention device I-2 | ITO/NPD(50)/99% 9 + 1% rubrene(30)/BAlq(30)/LiF/Al | 1.8% | 300 |
| | Invention device I-3 | ITO/NPD(50)/99% 15 + 1% rubrene(30)/BAlq(30)/LiF/Al | 2.1% | 270 |

TABLE 5

| | Device No. | Device constitution | External quantum efficiency | Running durability |
|---|---|---|---|---|
| Example J (as host material of phosphorrescence device) | Comparative device J-1 | ITO/NPD(40)/15% XIX-11 + 75% mCP + 10% Pt4(30)/BAlq(30)/LiF/Al | No light emission | Unmeasurable |
| | Comparative device J-2 | ITO/NPD(40)/15% HT-13 + 75% mCP + 10% Pt4(30)/BAlq(30)/LiF/Al | No light emission | Unmeasurable |

TABLE 5-continued

| | Device No. | Device constitution | External quantum efficiency | Running durability |
|---|---|---|---|---|
| | Invention device J-1 | ITO/NPD(40)/15% 1 + 75% mCP + 10% Pt4 (30)/BAlq(30)/LiF/Al | 8.4% | 80 |
| | Invention device J-2 | ITO/NPD(40)/15% 9 + 75% mCP + 10% Pt4 (30)/BAlq(30)/LiF/Al | 9.2% | 75 |
| | Invention device J-3 | ITO/NPD(40)/15% 22 + 75% mCP + 10% Pt4(30)/BAlq(30)/LiF/Al | 9.5% | 54 |
| Example K (for hole transport layer of fluorescence device) | Comparative Device K-1 | ITO/NPD(40)/XIX-11(10)/90% CBP + 10% Irppy(30)/BAlq(30)/LiF/Al | 2.2% | 11 |
| | Comparative device K-2 | ITO/NPD(40)/HT-13(10)/90% CBP + 10% Irppy(30)/BAlq(30)/LiF/Al | 2.1% | 19 |
| | Invention device K-1 | ITO/NPD(40)/16(10)/90% CBP + 10% Irppy(30)/BAlq(30)/LiF/Al | 10.0% | 117 |
| | Invention device K-2 | ITO/NPD(40)/1(10)/90% CBP + 10% Irppy(30)/BAlq(30)/LiF/Al | 10.2% | 100 |
| | Invention device K-3 | ITO/NPD(40)/23(10)/90% CBP + 10% Irppy(30)/BAlq(30)/LiF/Al | 9.3% | 121 |
| Example L (for electron transport layer of fluorescence device) | Comparative Device L-1 | ITO/NPD(50)/90% CBP + 10% Irppy(30)/ XIX-9(3)/BAlq(27)/LiF/Al | No light emission | Unmeasurable |
| | Comparative device L-2 | ITO/NPD(50)/90% CBP + 10% Irppy(30)/ HT-13(3)/BAlq(27)/LiF/Al | 3.1% | 45 |
| | Invention device L-1 | ITO/NPD(50)/90% CBP + 10% Irppy(30)/ 4(3)/BAlq(27)/LiF/Al | 12.1% | 136 |
| | Invention device L-2 | ITO/NPD(50)/90% CBP + 10% Irppy(30)/ 9(3)/BAlq(27)/LiF/Al | 11.9% | 135 |
| | Invention device L-3 | ITO/NPD(50)/90% CBP + 10% Irppy(30)/ 20(3)/BAlq(27)/LiF/Al | 12.8% | 144 |

Compounds used in Examples are shown below.

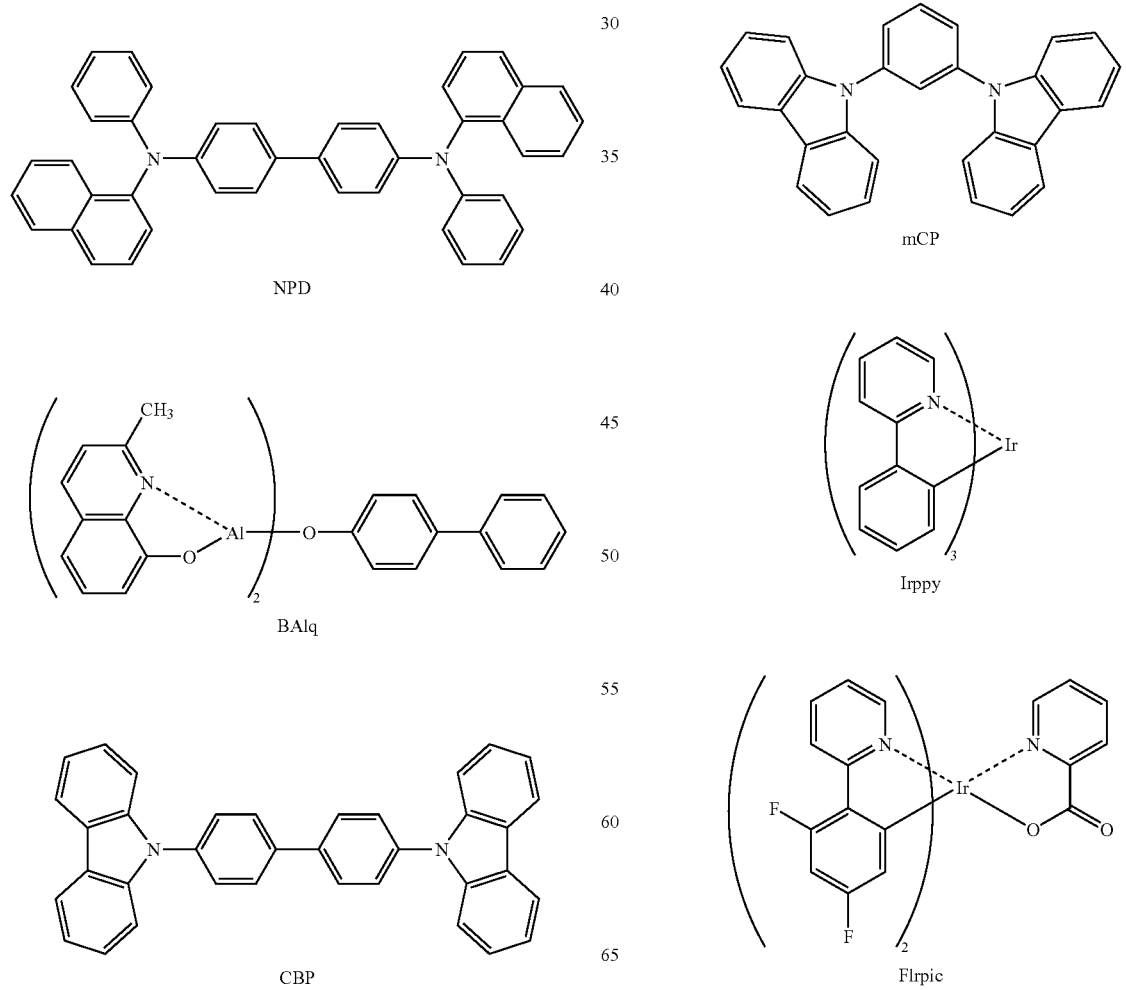

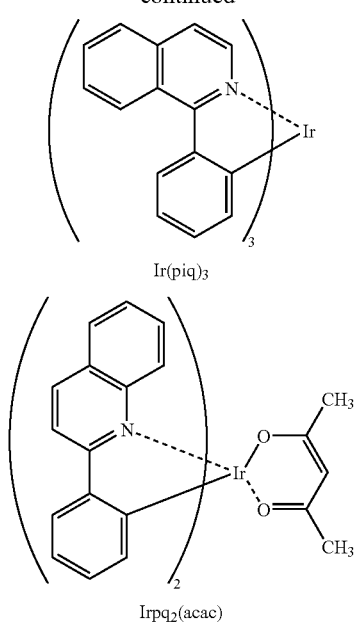
Ir(piq)₃
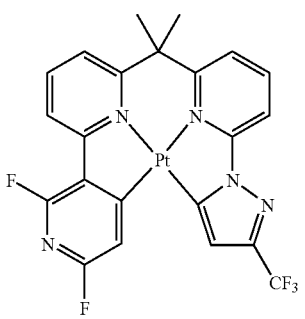
Irpq₂(acac)
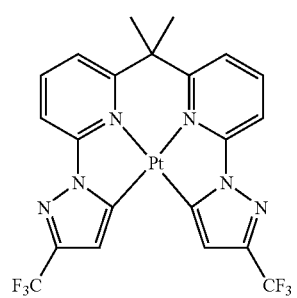
Pt1
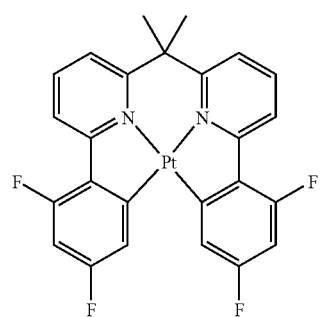
Pt2
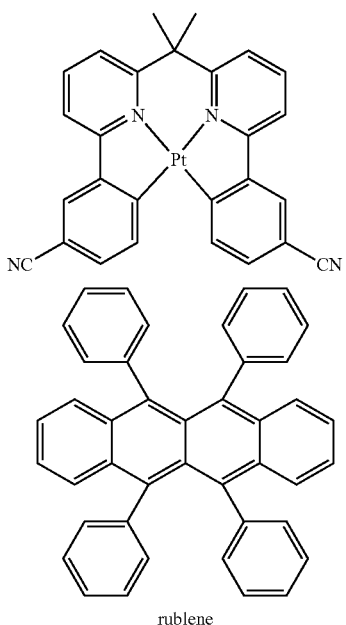
Pt3
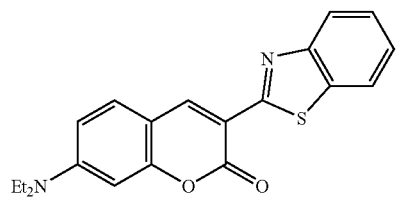
rublene
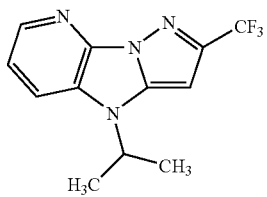
coumarine 6
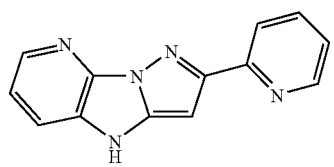
XIX-5
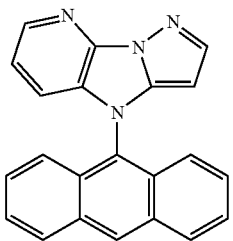
XIX-9
Pt4
XIX-11

-continued

HT-7

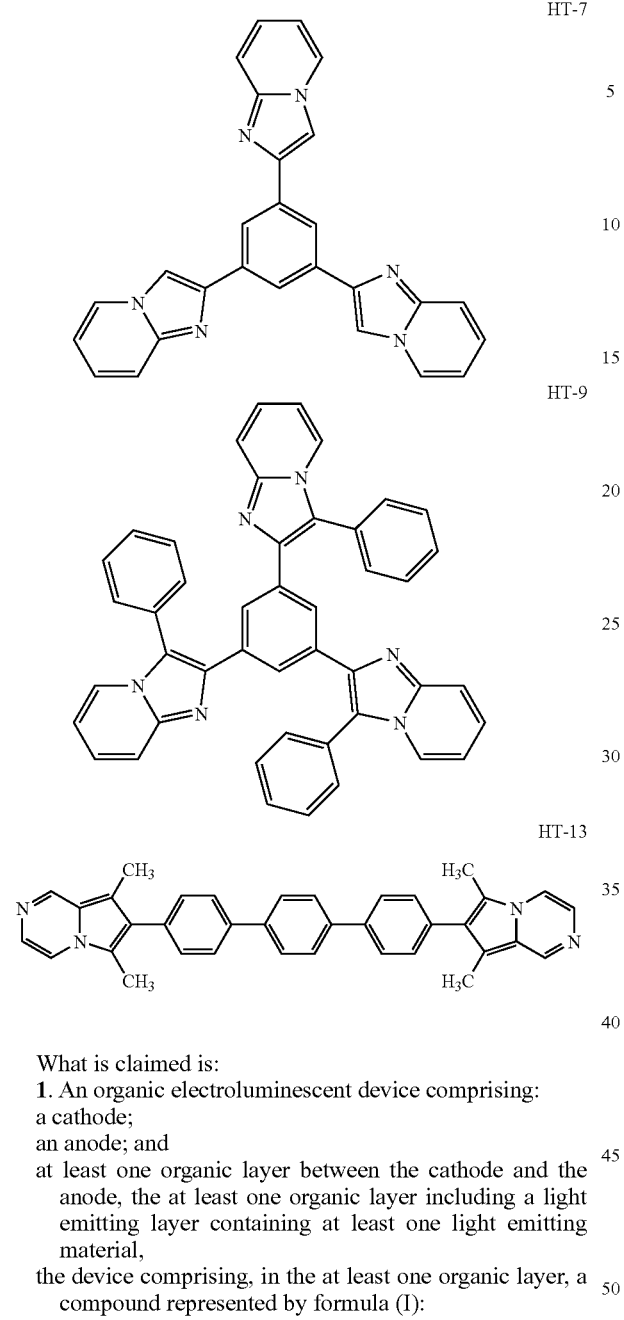

HT-9

HT-13

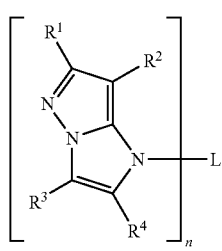

What is claimed is:

1. An organic electroluminescent device comprising:
a cathode;
an anode; and
at least one organic layer between the cathode and the anode, the at least one organic layer including a light emitting layer containing at least one light emitting material,
the device comprising, in the at least one organic layer, a compound represented by formula (I):

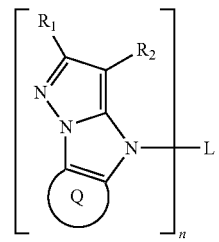

wherein n stands for an integer of 2 or 3, L represents an n-valent linking group, and $R^1$, $R^2$, $R^3$, and $R^4$ each independently represents a hydrogen atom or a substituent.

2. The organic electroluminescent device according to claim 1, wherein the compound represented by formula (I) is a compound represented by formula (II):

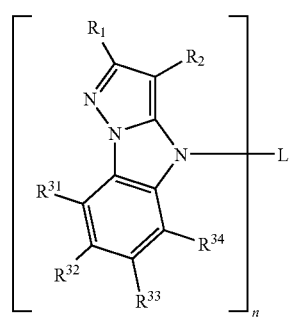

wherein n stands for an integer of 2 or 3, L represents an n-valent linking group, $R^1$ and $R^2$ each independently represents a hydrogen atom or a substituent, and Q represents a benzene ring or an aromatic heterocycle.

3. The organic electroluminescent device according to claim 2, wherein the compound represented by formula (II) is a compound represented by formula (III):

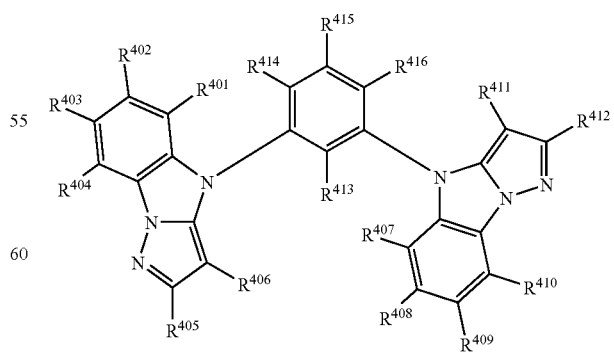

wherein n stands for an integer of 2 or 3, L represents an n-valent linking group, and $R^1$, $R^2$, $R^{31}$, $R^{32}$, $R^{33}$, and $R^{34}$ each independently represents a hydrogen atom or a substituent.

4. The organic electroluminescent device according to claim 1, wherein L in formula (I) represents a linking group including a benzene ring.

5. The organic electroluminescent device according to claim 3, wherein the compound represented by formula (III) is a compound represented by formula (IV):

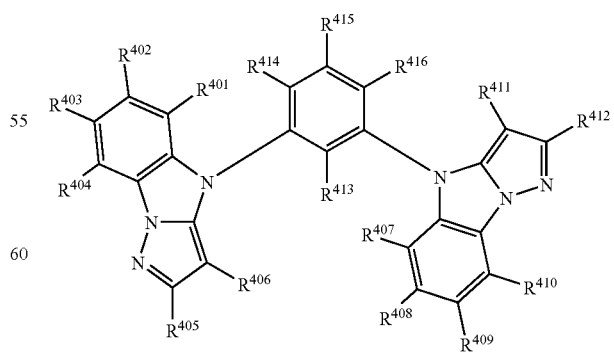

wherein $R^{401}$ to $R^{416}$ each independently represents a hydrogen atom or a substituent.

6. The organic electroluminescent device according to claim 1, wherein the compound represented by formula (I) is contained in the light emitting layer.

7. The organic electroluminescent device according to claim 1, wherein the light emitting material includes a phosphorescent material.

8. The organic electroluminescent device according to claim 7, wherein the phosphorescent material is a platinum complex or an iridium complex.

9. The organic electroluminescent device according to claim 8, wherein the platinum complex has a tridentate ligand or a tetradentate ligand.

10. The organic electroluminescent device according to claim 9, wherein the platinum complex is represented by formula (C-1):

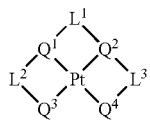

wherein $Q^1$, $Q^2$, $Q^3$, and $Q^4$ each independently represents a ligand coordinated to Pt, and $L^1$, $L^2$, and $L^3$ each independently represents a single bond or a divalent linking group.

11. A compound represented by formula (IV):

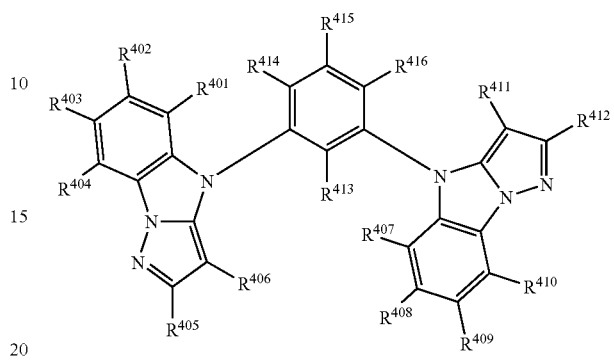

wherein $R^{401}$ to $R^{416}$ each independently represents a hydrogen atom or a substituent.

* * * * *